(12) United States Patent
Soller et al.

(10) Patent No.: US 6,304,767 B1
(45) Date of Patent: Oct. 16, 2001

(54) NON-INVASIVE OPTICAL MEASUREMENT OF BLOOD HEMATOCRIT

(75) Inventors: Babs R. Soller, Northboro; Ronald H. Micheels, Concord, both of MA (US)

(73) Assignees: Polestar Technologies, Inc., Needham Heights; University of Massachusetts, Boston, both of MA (US)

(*) Notice: Subject to any disclaimer, the term of this patent is extended or adjusted under 35 U.S.C. 154(b) by 0 days.

(21) Appl. No.: 09/452,232

(22) Filed: Dec. 1, 1999

Related U.S. Application Data

(62) Division of application No. 09/020,594, filed on Feb. 4, 1998, now Pat. No. 6,006,119.

(51) Int. Cl.$^7$ .................................................. A61B 5/00
(52) U.S. Cl. ............................................ 600/322; 356/39
(58) Field of Search ..................................... 600/310, 322, 600/323, 324; 356/39

(56) References Cited

U.S. PATENT DOCUMENTS

| | | |
|---|---|---|
| 4,033,330 | 7/1977 | Willis et al. . |
| 4,041,932 | 8/1977 | Fostick . |
| 4,975,581 | 12/1990 | Robinson et al. . |
| 5,277,181 | 1/1994 | Mendelson et al. . |
| 5,337,745 | 8/1994 | Benaron . |
| 5,355,880 | 10/1994 | Thomas et al. . |
| 5,372,136 | 12/1994 | Steuer et al. . |
| 5,385,539 | 1/1995 | Maynard . |
| 5,435,309 | 7/1995 | Thomas et al. . |
| 5,441,053 | 8/1995 | Lodder et al. . |
| 5,494,032 | 2/1996 | Robinson et al. . |
| 5,499,627 | 3/1996 | Steuer et al. . |
| 5,522,389 | 6/1996 | Fischer et al. . |
| 5,526,808 | 6/1996 | Kaminsky . |
| 5,553,615 | 9/1996 | Carim et al. . |
| 5,630,413 | 5/1997 | Thomas et al. . |

FOREIGN PATENT DOCUMENTS

| | | |
|---|---|---|
| 0 419 222 A2 | 3/1991 | (EP) . |
| 0 419 222 A3 | 3/1991 | (EP) . |
| 0 476 192 A2 | 3/1992 | (EP) . |

OTHER PUBLICATIONS

Benaron, "Optical Biopsy and Imaging Advance Medical Care," *Laser Focus World*, 79–87, Jan. 1994.

(List continued on next page.)

*Primary Examiner*—Eric F. Winakur
(74) *Attorney, Agent, or Firm*—Fish & Richardson, P.C.

(57) ABSTRACT

The invention provides an optical method and apparatus for non-invasively determining blood hematocrit. The method includes the step of first irradiating blood with optical radiation. Radiation reflected or transmitted from the blood is then collected to determine an optical spectrum. Hematocrit is then determined by comparing this spectrum to a mathmatical model relating optical properties to blood Hematocrit.

21 Claims, 22 Drawing Sheets

OTHER PUBLICATIONS

Benesch et al., "Equations for the Spectrophotometric Analysis of Hemoglobin Mixtures," *Anal. Biochem.* 55:245–248, 1973.

Drennen et al., "Near–Infrared Spectrometric Determination of Hydrogen Ion, Glucose, and Human Serum Albumin in a Simulated Biological Matrix," *Spectroscopy*, 6:28–34, 1991.

Dunn et al., "Experimental and Chemical Use of pH Monitoring of Free Tissue Transfers," *Anals. of Plastic Surgery*, 30:1–7, 1993.

Hampson et al., "Near Infrared Monitoring of Human Skeletal Muscle Oxygenation During Forearm Ischemia," *American Physiological Society*, 2449–2453, 1988.

Parsons et al., "Dynamic Mechanism of Cardiac Oxygenation During Brief Ischemia and Reperfusion," American Physiological Society, H1477–H1485, 1990.

Reeves, "Influence of pH, Ionic Strength, and Physical State on the Near–Infrared Spectra of Model Compounds," *J. of AOAC International*, 77:814–820, 1994.

Robinson et al., "Noninvasive Glucose Monitoring in Diabetic Patients: A Preliminary Evaluation," *Clinical Chemistry*, 38:1618–1622, 1992.

Snell et al., "A Convenient Spectroscopic Method for the Estimation of Hemoglobin Concentrations in Cell–Free Solutions," *J. Biochem. & Biophys. Methods*, 17:25–34, 1988.

Sobezynski, "Diode Arrays May Light Up Compact Spectrometers," *Laser Focus World*, 75–81, Mar. 1995.

Walt, "Fiber–Optics Sensors for Continuous Clinical Monitoring," *Proceedings of the IEEE*, 80:903–911, 1992.

Ward et al., "Post–Prandial Blood Glucose Determination by Quantitative Mid–Infrared Spectroscopy," *Applied Spectroscopy*, 46:959–965, 1992.

Vari et al., "Blood Perfusion and pH Monitoring in Organs Via Optical Biopsy," *Am. Soc. for Lasers in Surgery and Medicine Supplement*, 7:3, Abstract 10, 1995 (Apr.).

McNulty, Stephen E. et al., "Evaluation of STAT–CRIT® Hematocrit Determination in Comparison to Coulter and Centrifuge: The Effects of Isotonic Hemodilution and Albumin Administration," *Anesth Analg*, 1993;76:830–4.

Soller, Babs R. et al., "Feasibility of Non–Invasive Measurement of Tissue pH Using Near–Infrared Reflectance Spectroscopy," *Journal of Clinical Monitoring*, 12:387–395, 1996.

Cope, M. et al., "System for Long–Term Measurement of Cerebral Blood and Tissue Oxygenation on Newborn Infants by Near Infra–red Transillumination," *Med. & Biol. Eng. & Comput.*, 1988, 26, 289–294.

Steuer, Robert R. et al., "Instantaneous Changes in Circulating Blood Volume Due to Various Physiological Maneuvers," *Dialysis & Transplantation*, vol. 23, No. 11, Nov. 1994, p. 643.

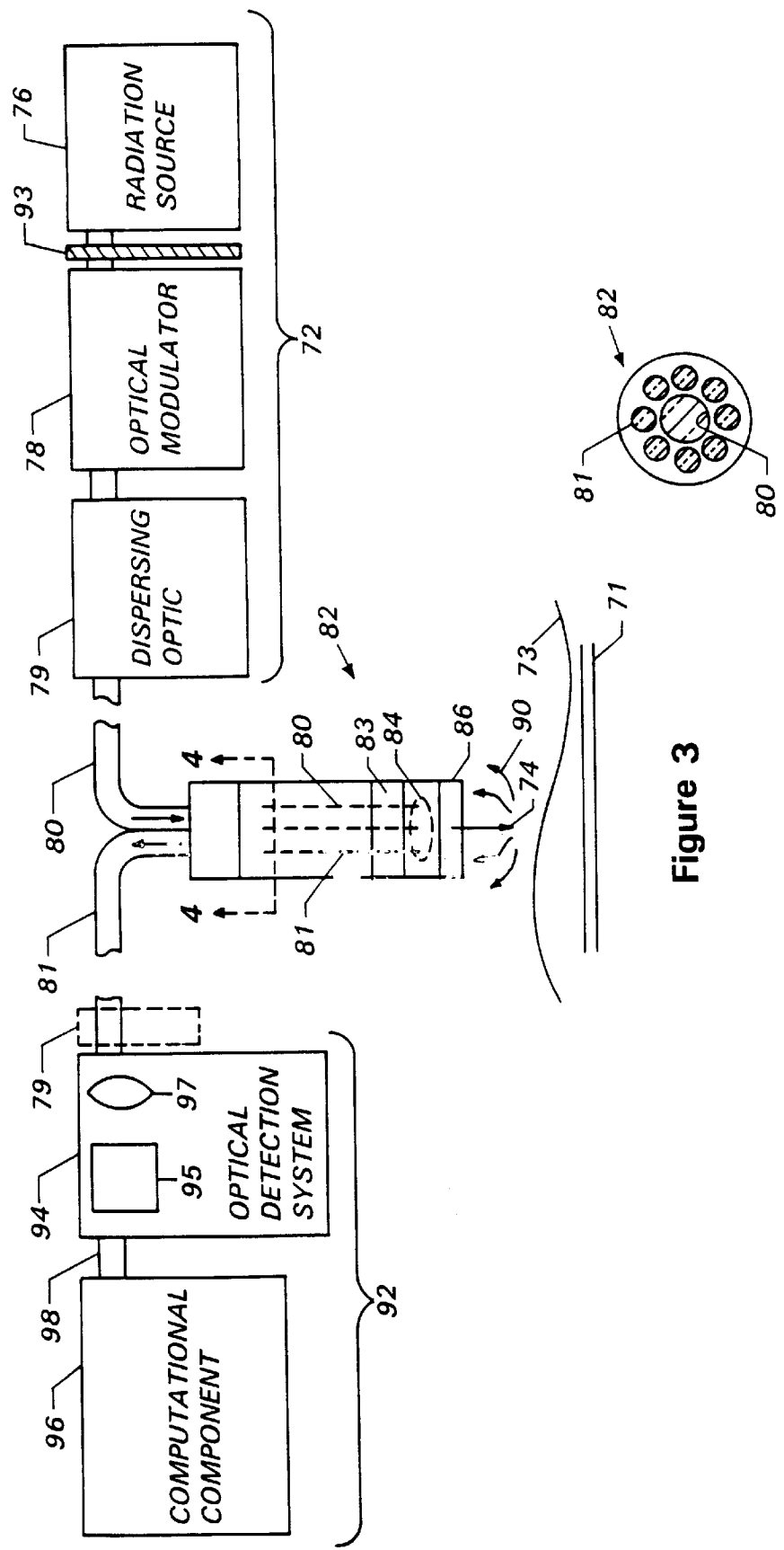

NON-INVASIVE OPTICAL MEASUREMENT OF BLOOD HEMATOCRIT

This is a divisional of U.S. application Ser. No. 09/020,594 filed Feb. 4, 1998, now U.S. Pat. No. 6,006,119.

STATEMENT AS TO FEDERALLY SPONSORED RESEARCH

The invention described herein was made in the performance of work funded in part by Small Business Innovation Research Grant No. DAMD17-98-C-8014 sponsored by the U.S. Army. The government may have certain rights in this invention.

BACKGROUND

This invention relates to measurement of blood hematocrit (Hct).

Hematocrit is the volume percent of red blood cells in a blood sample and is one of the most commonly performed blood tests. The standard method for measuring hematocrit involves collecting a blood sample in a capillary tube and centrifuging the tube to separate out the red blood cells from the plasma. By measuring the height of a resulting layer of red blood cells in the capillary and referencing it to the total blood volume, the volume percent of red blood cells can be quantified. Hematocrit measurements on blood samples are now often made with more automated techniques such as conductivity measurements.

Hematocrit can also be measured non-invasively. Two approaches have been reported for such non-invasive monitoring of hematocrit, an optical approach and an impedance method. Impedance methods are found to be inaccurate when protein and electrolyte levels are abnormal, such as when blood is replaced with crystalloid solutions, as would happen during resuscitation of trauma victims. All of the reported optical techniques are variations on oximetric methods where hematocrit is measured using only the concentrations of oxygenated and deoxygenated hemoglobin. The concentrations of oxygenated and deoxygenated hemoglobin are directly measured by absorption or reflection using 2 to 4 wavelengths of light in the near-infrared region of the hemoglobin spectrum.

SUMMARY

The invention provides a non-invasive optical and mathematical method to measure hematocrit with an accuracy of approximately 99%. The accuracy results from the complete analysis provided by the new optical method, which measures blood hematocrit by quantifying a plurality of red blood cell constituents.

In general, in one aspect, the invention features a method for determining blood hematocrit. The method includes irradiating blood with optical radiation having a selected range of optical wavelengths to produce an optical spectrum. The wavelengths in the selected range are affected by a plurality of red blood cell constituents. Hematocrit is determined by processing the optical spectrum with a mathematical model. The model is constructed by relating optical properties of the plurality of red blood cell constituents to known blood hematocrit.

Embodiments of this aspect of the invention may include one or more of the following features. The plurality of red blood cell constituents include all hemoglobins and cellular bodies, e.g., cellular nuclei and cellular membranes. The mathematical model is determined prior to irradiating the blood by processing optical spectra having known hematocrit values with a mathematical algorithm, such as a partial least-squares (PLS) fitting algorithm. Alternatively, this model can feature a non-linear mathematical equation relating hematocrit to a reflection or absorption spectrum taken from a plurality of red blood cell constituents. In particular, the optical spectra used to construct the model can be recorded on an extracted blood sample.

The optical radiation can be between 400 and 2000 nm. In particular, the radiation can be between 500 and 1100 nm. The optical spectrum can be produced by irradiating the blood in vivo or in vitro and then collecting radiation that is either reflected or scattered from a plurality of red blood cell constituents or transmitted through a plurality of red blood cell constituents.

In the processing step, the optical spectrum is compared with the mathematical model to determine the blood hematocrit.

According to another aspect of the invention, the invention features a device for determining blood hematocrit. The device includes an array of light sources for delivering radiation to the sample, each of which can deliver radiation at a unique range of optical wavelengths. The device also includes a power supply and a modulation system in electrical contact with each of the light sources. The modulation system is configured to modulate electrical power delivered from the power supply to each of the light sources. A detection system included in the device features a first optical detector and a plurality of second optical detectors. The first optical detector is configured to receive radiation from the sample. The plurality of second optical detectors is configured to receive radiation from each of the light sources.

After receiving the radiation, the first optical detector generates a first set of radiation-induced electrical signals, each corresponding to radiation emitted from a separate light source to the sample. The plurality of second optical detectors generates a second set of radiation-induced electrical signals, each corresponding to radiation emitted from a separate light source. A signal processor receives the first and second sets of electrical signals and, in response, generates first and second sets of digital, electrical signals. These signals are then received by a microprocessor. The microprocessor is programmed to process the signals to determine a first spectrum. The first spectrum (or a spectrum determined from the first spectrum) is then compared to a mathematical model to determine blood hematocrit. The detection system can further include phase-sensitive detection electronics in electrical contact with the first optical detector and the plurality of second optical detectors to detect radiation generated at the unique frequency. For example, the phase-sensitive detection electronics are incorporated in a lock-in amplifier.

Embodiments of this aspect of the invention can include one or more of the following features. The microprocessor can be programmed to calculate the mathematical model prior to processing the first set of digital, electrical signals. In addition, the radiation detected by the plurality of second detectors can be processed and used to determine a reference spectrum which, in turn, is used to calculate the reflection spectrum. Inclusion of the reference spectrum allows variations in the intensities of each light source to be taken into account. The signal processor and microprocessor can also perform signal averaging of the electric signals. In addition, the microprocessor is programmed to calculate the mathematical model before processing the first set of digital signals.

The plurality of second optical detectors can be equal to two. In particular, the plurality of second optical detectors can be equal to the number of light sources. For example, the device includes seven light sources. Each light source can be a light-emitting diode (LED) or a laser diode. The optical wavelengths emitted by the light sources are collimated by a molded lens array. In one embodiment, the optical wavelengths can be visible and near-infrared wavelengths. For example, the wavelengths can be 400 and 2000 nm, e.g., between 500 and 1100 nm. In particular, each light source delivers infrared radiation having a bandwidth of between about 0.1 and 100 nm. In addition, the light sources are adapted to deliver optical wavelength selected to be affected by the absorption and scattering from a plurality of red blood cell constituents.

In another aspect, the invention features a fiber optic device for determining blood hematocrit including an array of light sources for delivering radiation to the sample. The light sources are attached to a mount and a fiber optic cable is attached to each light source. The fiber optic cable includes a delivery fiber for delivering radiation to the sample, a reference fiber for delivering radiation to a detection system, a beam splitter for splitting light into the delivery fiber and the reference fiber, and a signal fiber for delivering radiation reflected by the sample to a detection system.

The detection system includes a first optical detector attached to the mount and coupled to the signal fiber for receiving radiation from the sample. The detection system also includes a second optical detector which is also attached to the mount and coupled to each reference fiber for receiving radiation directly from each of the light sources. The detection system, after receiving sample radiation, generates a first set of electrical signals, each corresponding to sample radiation delivered from a separate light source and received from the sample. The second optical detector, in response to the radiation, generates a second set of radiation-induced electrical signals, each corresponding to radiation delivered from a separate light source.

A signal processor is electrically coupled to the mount for receiving the first set of electrical signals and the second set of electrical signals. In response, the signal processor generates a first set of digital signals and a second set of digital electrical signals.

A microprocessor is configured to receive the first and second sets of digital signals to calculate blood hematocrit. The microprocessor is programmed to process the first set of digital signals to determine a sample spectrum and then compare the sample spectrum to a mathematical model to determine blood hematocrit of the sample.

Embodiments of this aspect of the invention may include one or more of the following features. The microprocessor can be additionally programmed to process the second set of digital electrical signals to determine a reference spectrum and then calculate a ratio between the reference spectrum and the first spectrum.

The fiber optic device can include a portion having a delivery fiber bundle surrounded by radially and symmetrically disposed signal fibers in a region where the fiber optic cable delivers radiation to the sample.

The invention has many advantages. In general, the new hematocrit measuring device allows facile measurement of blood hematocrit without the need to extract blood from a patient. Measurements made during surgery thus have minimal effect on the procedure at hand. Furthermore, hematocrit measurements can be made non-invasively by measuring the spectrum of the blood through the patient's skin. The non-contact measuring technique is desirable as it is safe and avoids the risk of infection either to the patient or health careworker. Measurements can also be made rapidly, and can thus be used on trauma patients and during surgical procedures to give the physician immediate feedback on the patient's condition. Measurements can also be made by a minimally skilled health care worker assisting in the evaluation of blood loss to trauma victims in remote, outdoor locations.

The hematocrit measuring device of the invention can be either hand-held or used with an endoscopic device. In both cases, the device is easily manipulated and can thus be used to measure hematocrit in hard-to-reach places.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein, including software User's Manuals, are incorporated herein by reference in their entirety. In case of conflict, the present application, including definitions, will control. In addition, the materials, methods, and examples are illustrative only and not intended to be limiting.

Other advantages will be apparent from the following detailed description, and from the claims.

BRIEF DESCRIPTION OF THE DRAWINGS

FIG. 3 is a schematic view showing one embodiment of a hematocrit measuring device.

FIG. 4 is a cross-sectional view of the delivery and signal cables used in the hematocrit measuring device of FIG. 3 taken along section line 4—4.

DETAILED DESCRIPTION

Figure 1:
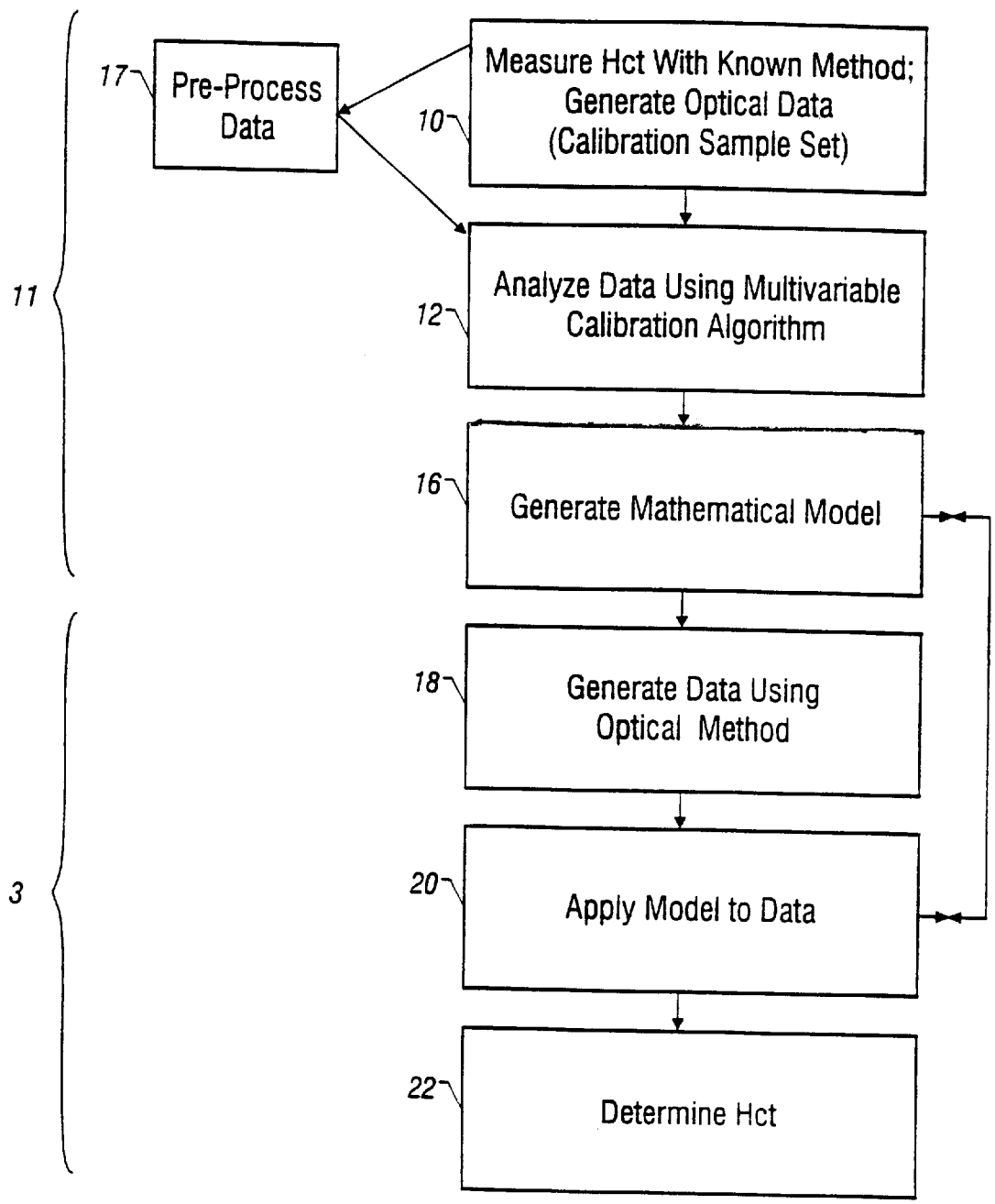
FIG. 1 is a flow chart showing the steps used for hematocrit measurement according to the method of the invention.

Hemoglobin constitutes approximately 90% of the red blood cell, and is mostly present in the oxygenated and deoxygenated forms. However, other forms of hemoglobin are also present in the red blood cell, including methemoglobin, carboxyhemoglobin and sulfhemoglobin. To accurately measure hematocrit, not only must these additional forms of hemoglobin be accounted for, but so must the remaining 10% of the cellular components, such as the nucleus and cell membranes, which do not contain hemoglobin. The invention provides an optical and mathematical method to measure hematocrit with increased accuracy relative to other methods, e.g., impedance and oximetric methods. The increased accuracy results from the more complete analysis provided by the new optical method, which measures blood hematocrit by quantifying all of the components of the red blood cells. The invention quantifies these additional blood cell components both by using a larger set of wavelengths in the measurement and by using a multivariate calibration technique. In addition, by using a larger set of wavelengths for analysis, the method compensates for variations in blood volume by accounting for factors relating to blood volume.

The invention is an accurate, small and easy-to-use hematocrit monitoring device using visible and near-infrared light including a set of wavelengths, e.g., 7 or more wavelengths, to record optical spectra of blood. The multi-wavelength spectra measured with this device are analyzed with multivariate calibration techniques, e.g., Partial Least Squares (PLS), to relate the reflected or transmitted light intensities to blood hematocrit determined by standard methods, e.g., the capillary tube method or a Coulter counter. This multivariate analysis approach accounts for all forms of hemoglobin as well as the additional cellular components that both absorb and scatter light and for changes in blood volume.

The hematocrit measuring-device of the invention is used to determine blood hematocrit in vivo, in vitro or ex vivo. In particular embodiments, the device can be used during critical care medical treatment to determine blood hematocrit.

In vivo blood hematocrit measurements are useful in neonatal care and for monitoring blood loss, e.g., in trauma victims. In addition, measurement of hematocrit is desirable for monitoring patients during resuscitation efforts and cardiopulmonary bypass surgery. Ex vivo blood hematocrit measurements are made on blood flowing through tubing for heart-lung and kidney dialysis machines.

A continuous, non-invasive, in vivo method of measuring hematocrit will provide a minimally skilled health care worker with an advanced method for monitoring trauma patients, yet reduce the risk of handling potentially infectious blood.

Non-invasive measurements can be made continuously or intermittently by health care workers in remote areas with minimal technical training. Hematocrit monitoring is particularly advantageous during patient transport.

In addition, hematocrit measuring devices can be used with minimally invasive surgical devices, such as endoscopes, to measure blood hematocrit. In vitro measurements are made on extracted blood samples to determine hematocrit.

Hematocrit Measuring Method

Blood hematocrit is measured in vivo, in vitro, or ex vivo by measuring and then processing optical data with a series of computational steps using a mathematical model. The optical data is a wavelength-dependent (or frequency-dependent) optical reflection or absorption spectrum covering a range of optical wavelengths (or frequencies). The wavelength dependence of the optical data is affected by the amount of absorption and scatter of a plurality of red blood cell constituents, e.g., all forms of hemoglobin, and all other cellular components, such as the nucleus and cell membrane. To accurately measure blood hematocrit, it is important that the range of optical wavelengths chosen includes the absorption and scattering affects of the plurality of red blood cell constituents.

The mathematical model relates actual blood hematocrit to optical data. The model is generated by taking optical spectra for a range of wavelengths affected by the plurality of red blood cell constituents from a number of samples at known hematocrit values, and then processing the spectra and the hematocrit values with a multivariate calibration procedure, e.g., a Partial Least Squares (PLS) fitting algorithm. The model is then used to determine the blood hematocrit of a blood sample, e.g., tissue containing blood, by measuring a reflection or Transmission spectrum from the blood, and then comparing the spectrum to the model. Multivariate calibration procedures incorporate information from a variety of chemical species and physical processes without having to measure separately the effect of each one. PLS accounts for all of the different red blood cell constituents, e.g., various forms of hemoglobin and other cellular bodies, by relating the optical measurements to a single parameter, hematocrit.

In particular embodiments, the device is used during critical care medicine to determine blood hematocrit.

Generating the Model

FIG. 1 shows a flow chart listing the processing steps used to determine blood hematocrit. The model is first generated with a series of steps (indicated by the bracket 11) and then stored, e.g., in a computer memory. The model is then accessed later in time and used in combination with a second series of steps (indicated by the bracket 13) to determine blood hematocrit.

To determine the model, optical data taken over a range of wavelengths, e.g., wavelengths affected by the plurality of red blood cell constituents, are generated from blood samples having varying blood hematocrit. The actual hematocrit, in turn, is measured with an acceptable reference method, e.g., centrifugal capillary hematocrit determination (step 10). The actual hematocrit, in particular, is determined by averaging multiple hematocrit measurements recorded by an acceptable reference method. Spectra for the model are taken from blood lying underneath a patient's skin, e.g., in a vein, artery or capillary, from blood containing tissue, or from extracted venous or arterial blood directly. In all cases, visible and near-infrared optical wavelengths are used to measure the spectra. Near-infrared wavelengths are particularly advantageous as they undergo minimal attenuation when passed through skin or covering tissue.

The actual blood hematocrit is recorded as a single numerical value, while the optical spectrum, e.g., a reflection or absorption spectrum, is in the form of an x-y array of points. The x values of the array represent particular optical wavelengths or frequencies, while the y values represent either reflectance or absorption intensities corresponding to these wavelengths or frequencies.

Absorption information can be determined from a reflection spectrum. The absorption spectrum ($A(\omega)$) can be calculated by taking the log of a reference spectrum ($I_b(\omega)$) divided by the sample reflection spectrum ($I_r(\omega)$), i.e.:

$$A(\omega)=\log [I_b(\omega)/I_r(\omega)] \quad (1)$$

The reference spectrum is obtained by measuring the reflectance spectrum of a highly reflecting reference material at the same sampling distance used when recording the sample reflection spectrum. Alternatively, a reference spectrum can be a sample spectrum taken under a particular smaple condition, i.e., normal or healthy condition.

It is desirable to pre-process the data (step 17) prior to processing with a numerical algorithm (step 12). For example, data containing large amounts of noise can be filtered using well-known smoothing algorithms to improve their signal-to-noise ratio. A particular smoothing algorithm is indicated by equation 2, below:

$$y_{i,ave} = \frac{1}{(n+1)} \sum_{j=i-n/2}^{j=i+n/2} y_j \quad (2)$$

where i is an integer value indicating a single data point (containing x and y values) in an x-y array. The intensity of the data point (i.e., $y_j$) is averaged together with the intensities of a well-defined set of neighboring data points ranging, for example, from $y_{i-n/2}$ to $y_{i+n/2}$, where n is an integer multiple of 2. The averaged intensity value ($y_{i,ave}$) is then recorded for the frequency or wavelength (i.e., $x_j$) corresponding to the intensity of the data point. This process is repeated for each data point in the x-y array. The degree to which noise and other features in the data are smoothed is increased as the number of neighboring data points (i.e., n) in the well-defined set is increased.

Any of a number of smoothing routines known in the art, such as the Savitsky-Golay algorithm, can also be used to increase the signal-to-noise ratio of the data. This and other conventional smoothing routines are described in "Numerical Recipes Example Book (C)" (second edition), (William T. Vetterling, eds., Cambridge University Press (1992)).

In other embodiments, the signal-to-noise ratio of the data is increased by averaging multiple sets of reflection spectra taken for a single hematocrit value. A conventional averaging algorithm is indicated by equation 3, below:

$$y_{i,ave} = \frac{1}{n_{ave}} \sum_{k=1}^{k=n_{ave}} y_{ik} \quad (3)$$

where $n_{ave}$ is the number of x-y arrays averaged together. k and i are integer counting variables indicating, respectively, a particular x-y array and a particular data point within the array. Thus, $y_{i=2,k=1}$ is the intensity of the second data point in the first x-y array. Averaging in this way improves the signal-to-noise ratio of the data by $(n_{ave})^{1/2}$. Thus, averaging together ten spectra improves the signal-to-noise ratio over a single spectrum by more than a factor of 3.

Mean-centering is another technique that can be used to pre-process the data prior to processing with the numerical algorithm. In this case, x-y arrays corresponding to different hematocrit values are averaged together as indicated by equation 3 to generate an average x-y array; the average x-y array is then subtracted from each individual x-y array taken at different hematocrit values:

$$\hat{y}_{ik}=y_{ik}-y_{i,ave} \quad (4)$$

In equation 4, the "hat" over $y_{ik}$ indicates the data point is normalized by the mean-centering operation. Other pre-processing routines include taking a first or second derivative of the spectra prior to processing, or making multiplicative scatter corrections to the spectra (see, e.g., H. Martens and T. Naes, "Multivariable Calibrations", J. Wiley & Sons (1989)).

Following pre-processing, a PLS algorithm is used to process the x-y arrays and corresponding hematocrit values (step 12) to generate a mathematical model. PLS algorithms are well-known for statistical analysis of x-y arrays of data points. Other regression algorithms, such as least-squares fitting and principal components regression, can also be used to generate the model. These algorithms are described in Thomas, "A Primer to Multivariate Calibration", *Analytical Chemistry*, 66:795–804 (1994). Preferably, a computer using a commercially available software package incorporating the PLS algorithm is used to process the input data. In preferred embodiments, the Grams/386 software package (Galactic Industries, Inc.) is used to perform the PLS analysis. Alternatively, a similar PLS algorithm can be coded directly into the computer. Such an algorithm is defined, for example, in "Numerical Recipes Example Book (C)," supra. The salient features of the algorithm are described below. A complete guide to the operation of the Grams/386 software is described in detail in the user's manual corresponding to the software package.

The PLS fitting algorithm-performs a statistical analysis on the input x-y arrays and known hematocrit values to determine a model relating reflection spectra to the sample's hematocrit. The algorithm is based on a statistical regressive analysis of the relationship between the reflection spectra in the form of the x-y arrays of data points and the hematocrit of the sample. This relationship is described by the following equation (5):

$$H_i = \sum_{m=1}^{M} (A_{im} \cdot R_{im}) \qquad (5)$$

where $H_i$ is the hematocrit of sample i, m is an index for the wavelengths measured in the x-y array, M is the total number of data points in the array, $R_{im}$ is the spectral reflectance (in units of log (1/reflectance)) for sample i at wavelength k, and $A_{im}$ are the PLS regression coefficients calculated by the PLS algorithm. Equation 5 is based on Beers Law, a relationship relating the measured absorbance of a sample to its concentration, absorption length, and extinction coefficient. Based on this equation, the PLS algorithm generates a mathematical model (step 16) similar to equation 5 above, wherein the regression coefficients are optimized to best fit the input data. The algorithm also generates other statistical information, described below, indicating the quality and accuracy of the model.

In a qualitative sense, the PLS algorithm determines small hematocrit-related changes in the reflection spectra and correlates these to the hematocrit value. The PLS algorithm interprets changes in each x-y array related to hematocrit, and generates a mathematical equation relating the reflection spectra to the predicted hematocrit value of the sample.

The numerical model is made as robust as possible. In general, this is accomplished by taking a large number of spectra at different hematocrit values and under different experimental conditions. The spectra and hematocrit values are then processed using the PLS algorithm as described above. Most preferably, the model is sensitive only to hematocrit-induced changes in the reflectivity of the blood, and is not affected by the presence of skin. Thus, when blood is not exposed either by a surgical procedure or by extraction, reflectivity measurements are made using optical wavelengths which are not strongly absorbed by the skin. In this way, the effects of scattering processes in the skin, which are not indicative of the underlying blood's reflectance properties, are minimized. In addition, the model is not sensitive to parameters associated with the optical measurement, e.g., slight changes in the optical power.

Visible and near-infrared reflection spectra can be collected to measure hematocrit anywhere where blood is within 5–10 mm of the skin surface, such as the inside of the wrist. Other possible sampling locations for the reflection measurement include arteries the eye, on the neck, on the palm, and on the bottom of the foot. Alternatively, measurements are made in transmission mode at locations currently used for pulse oximetry, such as through the finger or ear lobe. The effect factors such as, sample location, distance between sample and source, and changes in optical power is minimized by taking, during step 10, a variety of reflection spectra and corresponding hematocrit measurements using a variety of experimental conditions.

Moreover, the accuracy of the model is increased by taking measurements from a variety of blood samples. Hematocrit measurements taken from patients having different degrees of fat content, skin roughness and color, height, weight, blood type, and other characteristics can be analyzed and included in the model to increase its accuracy and reliability.

Preferably, a single, robust model which is invariant to different patients is determined prior to the optical hematocrit measurement. Alternatively, a range of different models can be determined and stored in the memory of a computer for later use. In this case, the appropriate model is selected according to the patient and used with optical spectra measured from the patient to determine hematocrit. Different models, for example, can correspond to patients having different temperatures, skin color, fat content, etc. As a particular example, temperature can be independently determined by a temperature sensor, e.g., a thermocouple or optical pyrometer, and then analyzed to select different models that are effective for different temperature ranges.

In addition, reflection or absorption spectra and hematocrit measurements for the model are taken from either solutions composed of chemical species typically found in blood, e.g., water, hemoglobin, or diluted solutions of extracted blood containing other chemicals often found in blood, or particles such as poly spheres that simulate the high scattering properties of blood cells. Such solutions have the advantage that their properties can be easily changed in a controlled manner, thereby allowing a large number of measurements to be taken under slightly different conditions.

Alternatively, a model based on only a few spectra and hematocrit measurements is determined for a particular patient undergoing a medical procedure. The optical hematocrit measuring device is used on the same patient along with the model during the remainder of the procedure to determine hematocrit.

The accuracy of the model can be further increased using statistical methods, such as cross-validation. In general, cross-validation is an algorithm (included in the Grams/386 software package in combination with PLS) which is used to develop the model with the best prediction capability and to obtain an objective assessment of the magnitude of prediction errors resulting from the model. Cross-validation involves removing a small subset of data, e.g., a spectrum and the corresponding known hematocrit value, from the entire data set, computing a calibration model from the new data set (entire data set minus the removed data), predicting hematocrit for the removed data, and comparing the predicted hematocrit to the known hematocrit. The removed data is returned to the data set and the entire cycle of removing, computing, predicting, and comparing is repeated for each subset of data, i.e., each spectrum with known hematocrit. The cross-validation algorithm calculates the differences between the predicted hematocrit and known hematocrit for the entire data set for a given model. Cross-validation is useful in computing and reporting the model with the lowest prediction error.

The software package also uses statistical tests to single out "outlier" x-y arrays which can decrease the accuracy of the model. Outlier arrays are erroneous data due to non-standard measurement conditions, such as the presence of fingerprints on the sample holder or a large drop in optical power. These data typically have dramatically different properties compared to data measured under more conventional measurement conditions, and thus decrease the accuracy of the hematocrit determination if included in the model. Similarly, outlier hematocrit values due to experimental deviations in the reference hematocrit measurements should not be used to calculate the model.

Optical data for a range of wavelengths are taken from the sample (step 18) using the optical hematocrit measuring device described below to determine blood hematocrit once the model is established and stored in a computer memory. Preferably, the device is the same as that used to measure data for the model. As described above, data are in the form of an x-y array of points, where y typically indicates the intensity of the optical measurement, e.g., the reflectivity, as a function of the x value which is frequency or wavelength. Measurements from the sample are then multiplied with the PLS regression coefficients of the model (step 20) as indicated by equation 4 to determine blood hematocrit (step 22).

Figure 2:
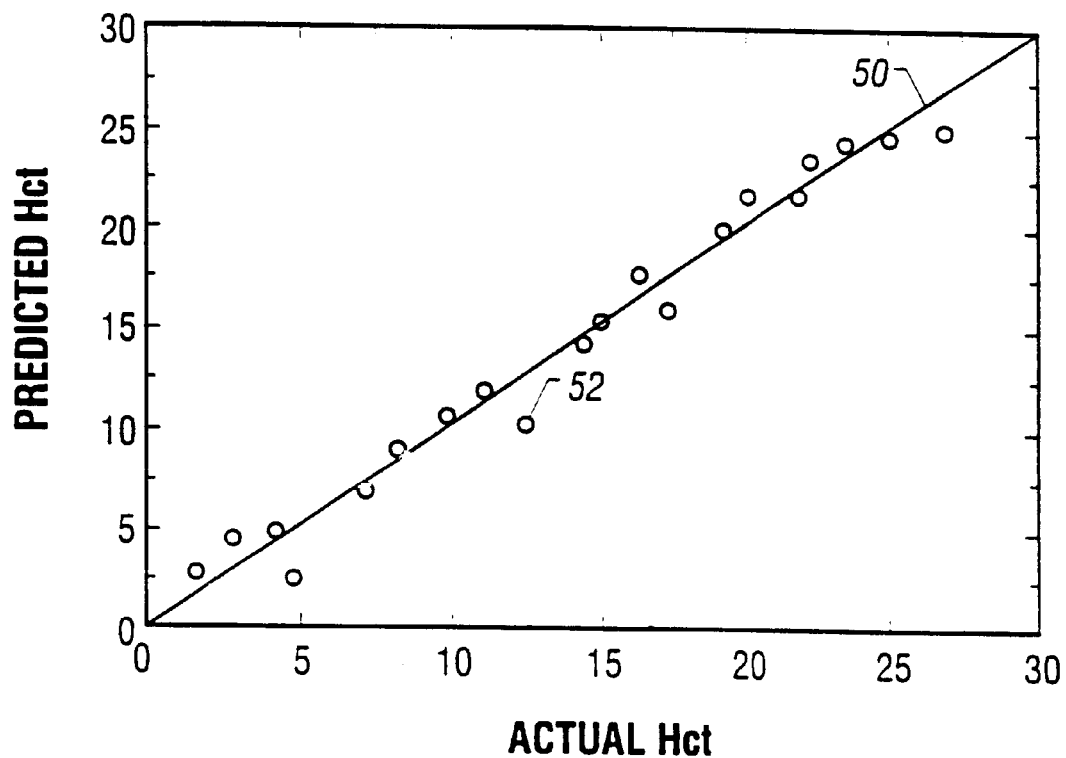
FIG. 2 is a plot of predicted hematocrit as a function of actual hematocrit representative of data generated by the new hematocrit measuring system.

FIG. 2 shows a representative graph plotting the predicted hematocrit as determined by the model as a function of the actual hematocrit generated using the cross-validation procedure. The line 50 indicates the cases where the hematocrit values predicted by the model are identical to the actual hematocrit. The data points 52 on either side of the line indicate individual hematocrit measurements made with the optical hematocrit measuring device and processed according to the invention.

The graph is a visual means for determining the accuracy of the model; the separation of the data points from the solid line is decreased as the accuracy of the model is increased. This accuracy can be mathematically represented by the standard error of prediction (SEP) of the model. This quantity describes the difference between the actual hematocrit and the value predicted by the model. Most preferably, the SEP is as small as possible. An R Squared Correlation Coefficient ($R^2$) is a probability value also used to mathematically indicate the accuracy of the model. If the predicted hematocrit is identical to the actual hematocrit, the probability value of the model is perfect. In this case, $R^2=1$, i.e., all points fit the model exactly. A SEP of better than 1% of hematocrit is desirable. $R^2$ and SEP are defined mathematically in equations 6 and 7, below:

$$R^2 = \frac{\sum_{i=1}^{n}(Yp_i - \hat{Y}k)^2}{\sum_{i=1}^{n}(Yki - \hat{Y}k)^2} \quad (6)$$

$$SEP = \sqrt{\frac{\sum_{i=1}^{n}(Yk_i - Yp_i)^2}{n}} \quad (7)$$

where Yk is the measured hematocrit, Yp is the predicted hematocrit, n is the number of spectra, and the "hat" indicates an average value for the measured hematocrit.

Hematocrit Measuring Devices

FIG. 3 shows an optical hematocrit measuring device 70 for determining blood hematocrit of a sample 71, e.g., blood in vessels underlying the skin 73. The device 70 features an illumination component 72 for generating radiation 74. Radiation 74 is used to measure the optical properties of the sample. The illumination component 72 includes a radiation source 76 to generate radiation, which is preferably a broad-band source, such as an arc lamp or tungsten halogen lamp. Alternatively, the radiation source is a laser, LED, or any other device capable of generating optical radiation over a range of wavelengths. For example, the illumination component 72 contains an optical filter 93 immediately after the radiation source 76. Optical filter 93, e.g., a band pass filter or a long wavelength pass filter, prevents radiation of undesirable wavelengths from reaching components 72 and 92.

The radiation is emitted in the visible and near-infrared spectral region. For example, the radiation has wavelengths from 400 nm–2000 nm, from 500 nm–1100 nm, or from 700 nm–1000 nm as the latter wavelength range is not significantly absorbed by skin. The depth of penetration into skin for optical wavelengths in the later range is about 7 mm. It is thus possible to propagate an optical beam at this wavelength range through the skin and into the vein, artery, capillary, or other blood containing tissues to determine the blood reflection spectrum.

Prior to irradiating the sample 71, the radiation 74 oasses through an optical modulator 78. The modulator can be any device that modulates the temporal or spatial properties of the radiation to facilitate measurement of the sample's optical properties. For example, the modulator 78 can be a spatial filter or lens system which improves the spatial mode of the radiation. In addition, the modulator 78 can include an optical chopper that modulates the time-domain optical properties of the radiation, or a device to modulate the electric power driving the light source.

The radiation 74 can be additionally transformed with a dispersing optic 79 before irradiating the sample. Alternatively, the dispersing optic is placed after the sample. In this case, the dispersing optic is preferably placed immediately before the detector. The dispersing optic is any device that permits separation of the different wavelengths of the radiation source, spatially or temporally to define an optical spectrum. The dispersing optic is preferably an optical diffraction grating. This device spatially disperses the frequencies of the radiation. The dispersing optic can be rotated, e.g., mechanically rotated, and used in combination with a spatial filter and small-area detector so that individual frequencies of the reflection spectrum can be measured in a point-by-point fashion. More preferably, the dispersing optic is used in combination with a detector array, such as a charge-coupled device (CCD) or photodiode, capable of simultaneously measuring a large bandwidth of frequencies.

The radiation is delivered via an optical delivery cable 80 to a probe 82 positioned in close proximity to the skin 73. For example, the probe can be held to contact the skin. The cable 80 is secured in the probe 82 using a cable clamp 83. The probe 82 is preferably a hand-held unit which is easily manipulated by the operator. A lens system 84 is included in the probe for focussing the radiation onto the sample. In addition, a heater 86 can be included to prevent moisture condensation on the lens system 84.

During operation, the radiation passes through the delivery cable 80, through the probe, and onto the sample. Reflected radiation 90 from the sample passes through the lens system 84 and through signal cable 81 which is joined to the delivery cable 80 at the cable clamp 83. The signal cable 81 delivers the reflected radiation 90 through the probe 82 and into an optical signal analysis system 92 for analysis.

The optical signal analysis system 92 includes an optical detection system 94 for detecting the optical signal, and a computational component 96 for processing the optical signal as described above. The optical detection system 94 includes a detection lens or mirror system 97 which images radiation onto a radiation-sensitive optical detector 95, such as a CCD or photodiode. The detector generates an electrical signal in response to the radiation which passes through an electrical connector 98 to the computational component 96. The electrical signal is an analog or digital representation of the x-y array of data points described above. For example, the computational component is a computer programmed to process the electrical signal using the method described herein. Alternatively, the dispersing element 79 may be placed between the optical detector 95 and the delivery end of the signal cable.

The optical component 72 and signal analysis system 92 of the hematocrit measuring device are provided, e.g., in a commercially available visible and infrared optical spectrometer. Such spectrometers are available, for example, from Ocean Optics, Analytical Spectral Devices, Near Infrared Systems, and Control Development.

FIG. 4 shows a cross-sectional view of the probe 82 which includes the optical delivery cable 80 and the signal cable 81. Cables 80, 81 may contain single strands of optical fibers or fiber optic bundles, each containing multiple optical fibers. For example, the optical fiber from the delivery cable is disposed near the center of the probe, and the optical fibers from the signal cable are disposed radially from the center. One or more additional signal cables can be included in the probe to increase the amount of radiation delivered to the signal analysis system. Typically, the optical delivery and signal fibers have diameters of between about 0.1 and 2 mm, and 10 to 500 microns, respectively.

Figure 5:
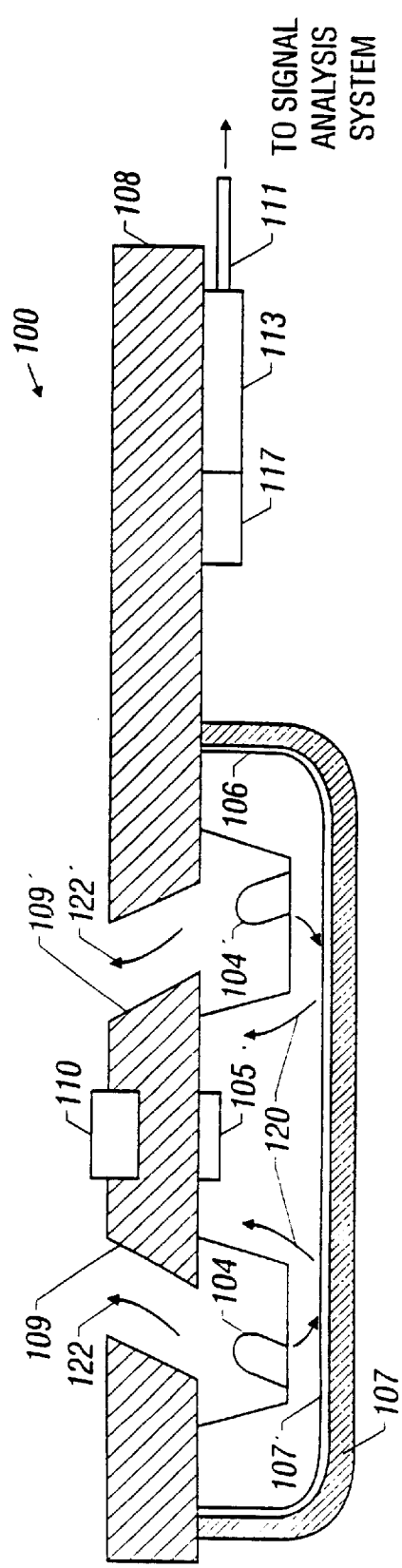
FIG. 5 is a cross-sectional view of an integrated hematocrit measuring device.
Figure 6:
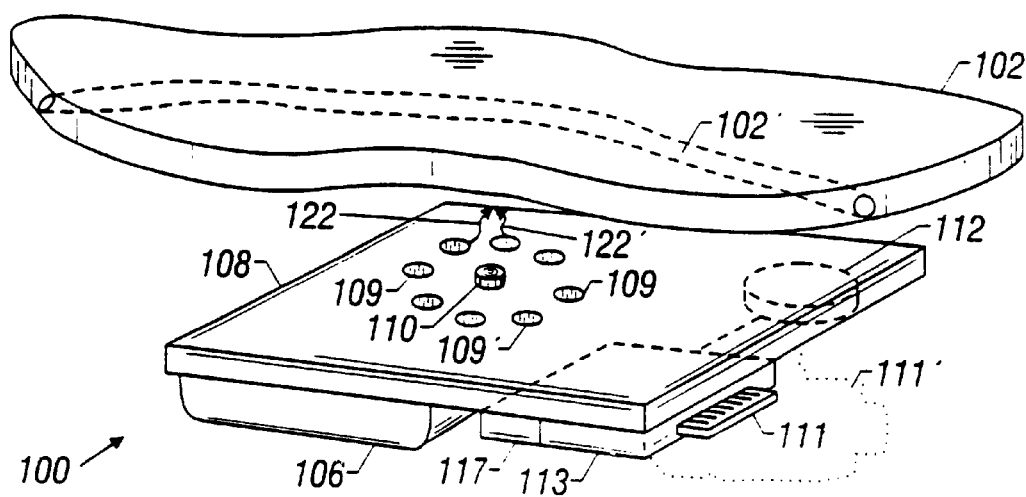
FIG. 6 is a perspective view showing the integrated hematocrit measuring device of FIG. 5 measuring a sample.

FIGS. 5 and 6 show an integrated, self-contained hematocrit measuring device 100 for measuring a reflection spectrum from a sample 102, e.g., tissue containing a blood vessel 102'. The hematocrit measuring device 100 features an array of, e.g., eight light-emitting diode (LED) radiation sources 104, 104', for providing optical radiation. Each LED in the array emits radiation having a different central visible or near-infrared wavelength. The bandwidth of radiation from each LED is typically between about 10 and 100 nm. In this way, the radiation from the sequence of LEDs in the array effectively covers the same range as a broad-band visible and near-infrared optical source. For example, the LEDs collectively emit radiation in the range of 500–1100 nm. Reflection spectra taken in this range can then be processed with the above method to determine the sample's hematocrit.

The LEDS are mounted inside a metalized reflective cover 106. The cover 106 is preferably composed of metal or plastic, which is coated on its inner surface 107 with a reflective material 107'. For example, the reflective material can be a metal or dielectric optical coating. A cover made from a reflective metal without a coating is also possible.

The cover 106 is attached to a mounting plate 108. The mounting plate 108 includes a series of portholes 109, 109' positioned above each LED so that radiation 122, 122' can pass through the mounting plate 108 and onto the sample. For example, the hematocrit measuring device includes between 5 and 20 LEDs. A single porthole is preferably included for each LED. The LEDs are preferably tilted inward so that radiation leaves the device at an angle relative to the mounting plate. In this way, each LED can irradiate approximately the same part of the tissue, hereby increasing the accuracy of the measurement. Alternatively, the LEDs can be leveled so that radiation is emitted upwards in a vertical direction. In both cases, the LEDs and portholes are evenly spaced and arranged in a circular pattern on the cover 106 and mounting plate 108, respectively.

The device 100 includes interior detectors 105 and exterior detectors 110 for detecting radiation. Typically, both the interior and exterior detectors include photodiodes and detection electronics, such as preamplifiers and electrical circuits for gated or phase-sensitive detection, for generating analog electrical signals in response to visible and near-infrared optical radiation. The exterior reflection detector 110 is attached to the outer surface of the mounting plate. During operation, optical radiation 122, 122' from each LED is emitted in all directions. A majority of the radiation 122, 122' passes through the portholes 109, 109' and through skin onto the sample 102. This radiation is partially reflected by the sample towards the exterior reflection detector 110 for detection.

The interior detector 105 is attached to the bottom surface of the mounting plate 108. As the sample is irradiated, a portion 120 of the radiation emitted by the LED propagates to the reflective cover 106 and is reflected by the reflective material 107' towards the interior detector 105. In this way, the interior detector 105 monitors the optical output emitted from the LEDs. The air space between the reflective cover and the mounting plate which surrounds the LEDs can be filled with an optically transparent polymer encapsulant. This material increases the device's resistance to mechanical shock and vibrations. Radiation detected by the interior detector is used to determine a reference spectrum which allows intensity variations from the various LEDs to be accounted for. The actual reflectivity spectrum is calculated by taking the ratio of the reflected radiation, as measured with the exterior reflection detector, to the reference spectrum, as measured with the interior detector.

A signal processor 113, power supply 112, and modulation system 117 are connected directly to the mounting plate 108. Alternatively, the signal processor 113, power supply 112 and modulation system 117 are mounted separately from the mounting plate 108. The power supply 112 supplies electrical power to the LED radiation sources and the interior and exterior detectors. Prior to being supplied to the LEDs, electrical power passes first through the modulation system 117. The modulation system 117 then applies an interval of periodic square wave, sine wave, or pulse modulated power so that each LED receives power and emits radiation during a separate time period. The time periods are temporally offset so that individual LEDs in the array emit radiation in a time-dependent, sequential manner with only one LED on at one time. Radiation reflected from the sample will thus arrive at the exterior detector during separate time periods corresponding to those when the LEDs are powered.

Alternatively, electrical power supplied to each LED can be modulated at a different frequency by the modulation system. This, in turn, drives each LED to emit radiation at a different modulation frequency. (Note that the modulation frequency is not the optical frequency of the radiation emitted from the LED.) Radiation reflected from the sample has the same frequency as the LED's modulation frequency. In this case the LED sources can bem ade to emit simultaneously.

In both cases, the radiation-induced analog electrical signals generated by the interior and exterior detector are sent to the signal processor 113 for analysis. When the incident radiation is modulated in a sequential, time-dependent fashion, the signal processor separates the individual signals of each LED measured by both the interior and exterior detectors. Alternatively, an external computer is used to control the sequenced powering of the LEDs and to separate the signals for the different LEDs. When the incident radiation is modulated at different frequencies for each LED, the signal processor separates the signals occurring at different modulation frequencies. The signals are then amplified and digitized with conventional analog-to-digital electronics contained within the signal processor. Alternatively, the signals from exterior reflection detector 110 and interior detector 105 is digitized with an analog-to-digital converter as the first step in the signal processor 113. Subsequent processing of the digitized signals takes place in a microprocessor included in the signal processor or in an external computer microprocessor.

In all cases the signal processor provides demodulation and signal averaging functions. The signal averaging function involves synchronously acquiring an effective signal for each cycle of the LED source modulation (square or sine wave, or pulse) and then averaging these single cycle signals over two or more cycles, e.g., over 100 to 10,000 cycles. For sine or square wave LED source modulation the demodulation and signal averaging functions are provided by a lock-in amplifier in the form of a electrical circuit or a digital algorithm. The digital algorithms are performed in either a microprocessor that is incorporated into the signal processor 113 or in an external computer connected to the signal-processor 113 through output connector 111.

Typically, the power supply 112, e.g., a battery, provides both positive and negative voltages of between about 2.5 and 12 V, and a current of between about 5 and 500 mA. The LED power can be modulated in the frequency range of 100 Hz to 10 kHz. For the sequential power case, the LEDs will be turned on for intervals in the 0.1–5 second range. In the case of pulse modulation, the frequency range will be the same as for sine or square wave modulation, but the pulse duty factor will be in the range of 0.01–10% of the modulation cycle time. Standard electrical batteries and circuits known in the art can be used for these purposes. Alternatively, a function generator and signal amplifier can be used to generate the frequency-modulated signal at the appropriate voltage and current. Alternatively, batteries can be replaced with a DC power supply which obtains pwoer from a standard AC power source, e.g., 120 VAC from a wall socket or from a computer power supply.

Once separated, amplified, and digitized, the signals can be sent through an output connector 111 to a computer for processing. The computer assembles the optical spectrum from the ratio of the reflection signal generated by the exterior detector divided by the reference signal generated by the interior detector. The final spectrum can then be displayed and analyzed as described above with the computer to determine the sample's hematocrit.

In another embodiment, a separate microprocessor 111' is included directly in the hematocrit measuring device. Microprocessor 111' receives the radiation-induced signals from the signal processor to calculate the reflection spectrum. The reflection spectrum can then be further analyzed to calculate the hematocrit of the sample using the method described above. This embodiment can be used to determine the hematocrit of the sample without using an external computer, and is thus particularly desirable for applications necessitating a portable or hand-held device.

To minimize size and facilitate operation, the LEDs of the integrated hematocrit measuring device are preferably patterned directly onto a printed circuit board (or other substrate) using standard integrated, hybrid, or printed circuit fabrication techniques. The signal receiving system, power supply, and optical modulation system can be attached to the circuit board using epoxy or equivalent adhesive materials, in addition to solder used to bond the electrical connections.

Because of its small size, the integrated device is portable, hand-held, and easily manipulated. This allows the operator to measure hematocrit in hard-to-reach places on a particular patient. Hematocrit can also be measured in remote locations, such as in an ambulance or outdoors. The integrated device also can be used as a body-worn sensor for continuous monitoring of hematocrit.

Figure 7:
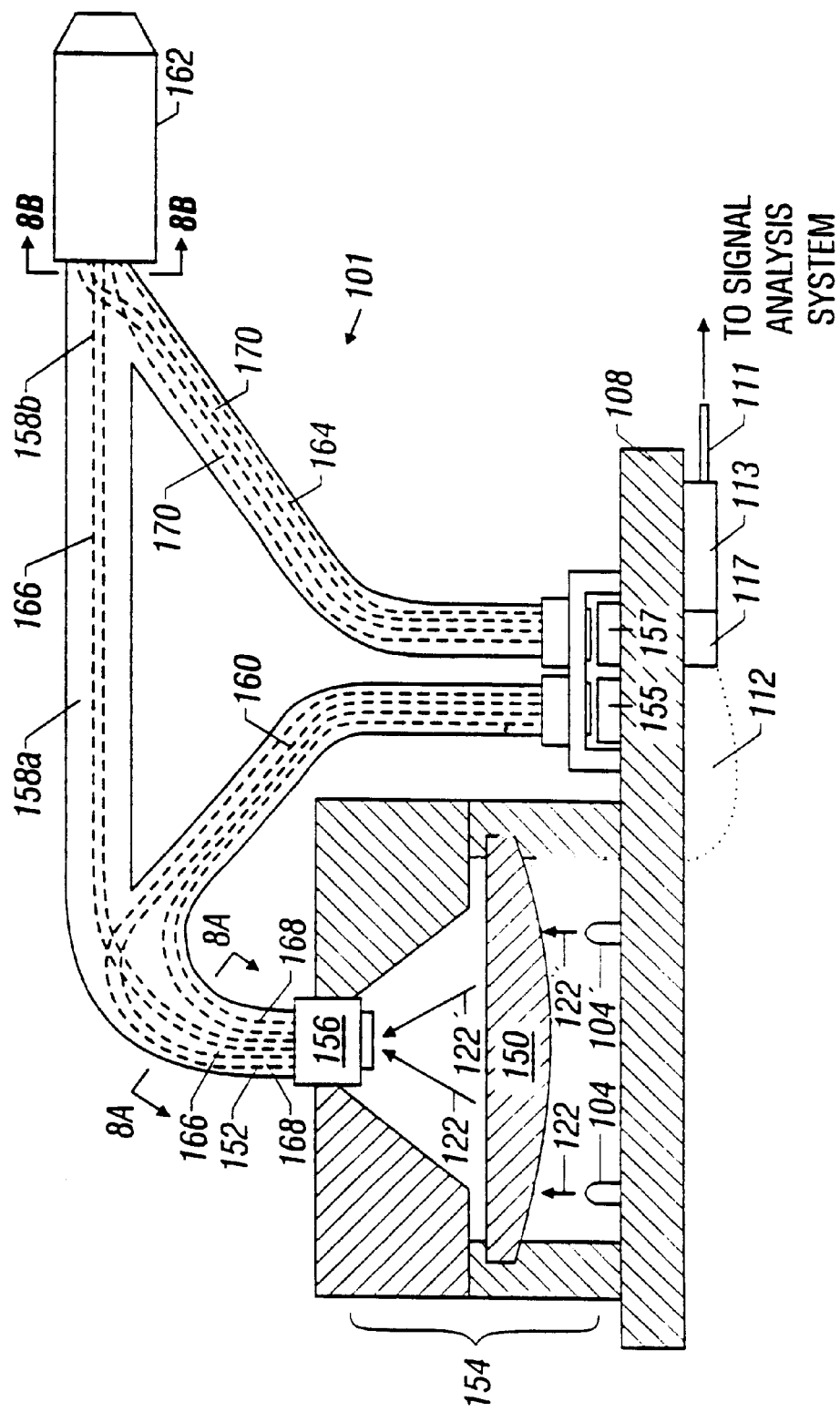
FIG. 7 is a cross-sectional view of an alternate embodiment of an integrated hematocrit measuring device.

FIG. 7 shows another embodiment of an integrated hematocrit measuring device 101 wherein radiation 122, 122' from the LEDs 104, 104' is focussed by a lens 150 into a fiber optic cable 152. A lens housing 154 attached to the mounting plate 108 is used to support both the lens 150 and an annular fiber housing 156 disposed radially around the fiber optic cable 152. In this embodiment, the LEDS 104, 104' are mounted directly on the mounting plate 108, and the device does not include a reflective cover.

The power supply 112 and modulation system 117 described above are used to modulate radiation from the LEDs as a function of time or frequency. The modulated radiation is then processed with the signal processor 113 as described above so that reference and reflection spectra can be ratioed. Spectra are processed with a microprocessor in the device to determine the sample's hematocrit. Alternatively, the spectra can be sent through the output connector 111 to an external computer for processing.

Figure 8A:
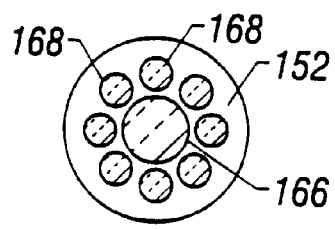
FIGS. 8A and 8B are cross-sectional views of a fiber optic cable of FIG. 7 taken along section lines 8A—8A and 8B—8B, respectively.

The fiber optic cable 152 is bifurcated at a first point 158a to deliver a portion of the incident radiation through a first fiber optic cable section 160 to a reference detector 155. This radiation is then processed to determine the reference spectrum. Accordingly, as shown in FIG. 8A, a cross-sectional slice of the fiber optic cable 152 immediately after the fiber housing 156 features a delivery fiber 166 surrounded by radially and symmetrically disposed reference fibers 168. During operation, radiation from the LEDs is focussed by the lens into both the delivery 166 and reference fibers 168. Radiation from the delivery fiber passes through the cable and onto a sample, while radiation coupled into the reference fibers propagates through the first fiber optic cable section 160 and onto the reference detector 155.

Figure 8B:
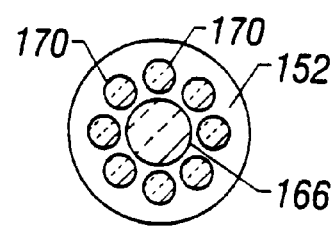

The radiation delivered by the fiber optic cable passes through a probe 162 prior to irradiating the sample. FIG. 8B shows a cross-sectional slice of the fiber optic cable 152 immediately before the probe 162. Here, a series of signal fibers 170 are radially and symmetrically disposed around the delivery fiber 166. In addition, the cable is bifurcated at a second point 158b. During operation, radiation reflected by the sample is collected by the signal fibers 170 and delivered through a second cable section 164 to a signal detector 157. This radiation is then processed as described above to determine the reflection spectrum.

Both the reference 168 and signal 170 fibers are preferably disposed around the delivery fiber 166 in a radial, symmetric pattern to maximize the coupling efficiency of, respectively, the incident and reflected radiation. Use of multiple fibers also facilitates optimal collection of radiation.

Figure 9:
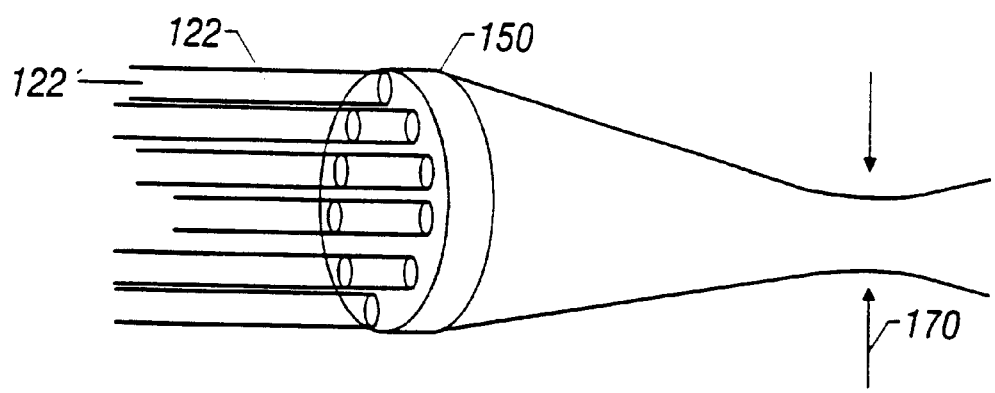
FIG. 9 is a perspective view of a lens in the device shown in FIG. 7 being irradiated by a series of LEDs.

FIG. 9 shows a preferred orientation of the lens 150 of FIG. 7 relative to the incident radiation 122, 122' generated by the LEDs. Preferably, the LEDs are arranged in the integrated optical device so that the incident radiation irradiates the lens in a symmetric, ring-like pattern disposed radially around the center of the lens 150. The component of the light from each LED that is collimated will be focused by the lens into a small spot at the entrance end of cable 52, thereby maximizing the amount of radiation coupled into the fiber optic cable.

Figure 10A:
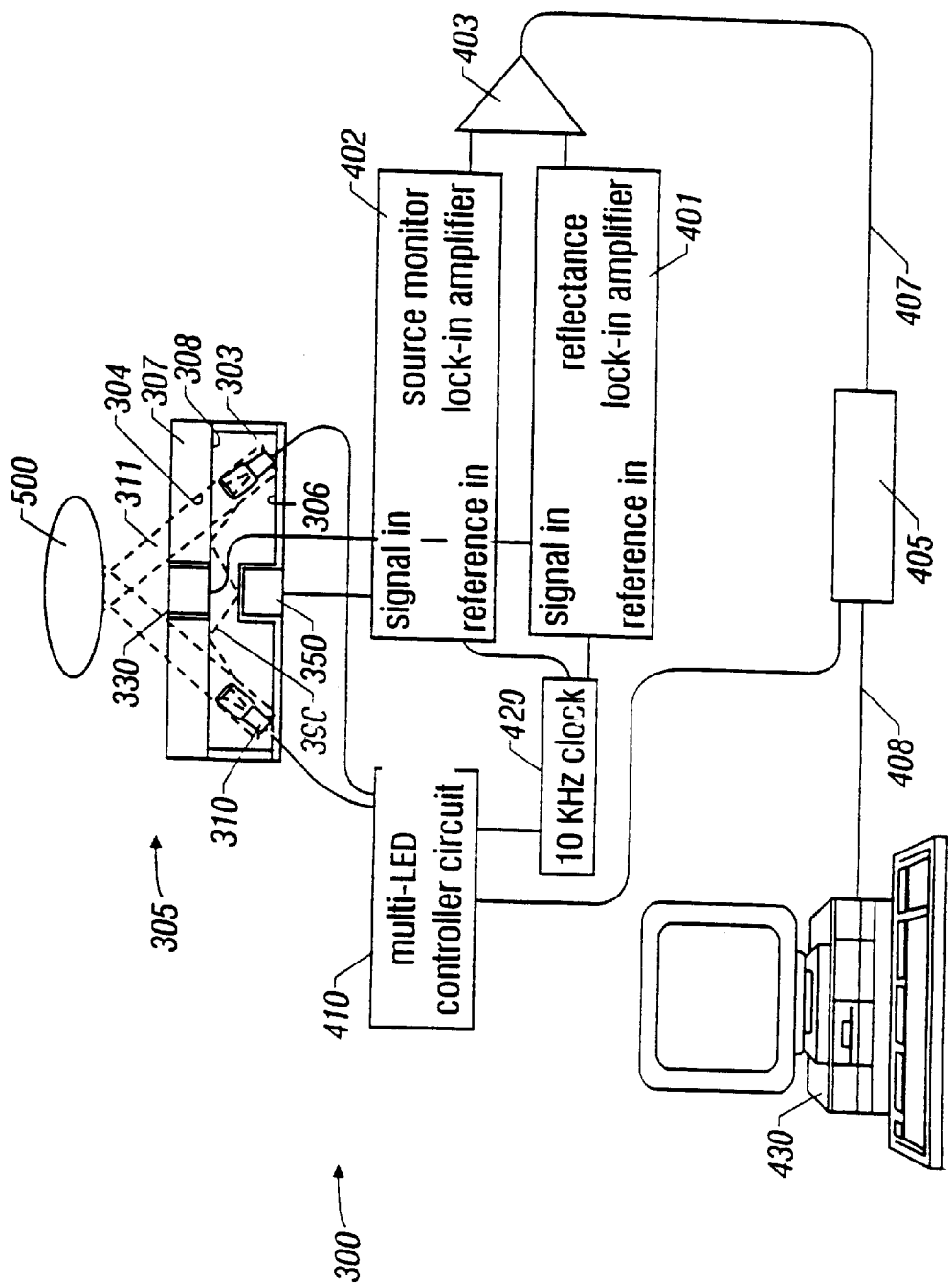
FIG. 10A is a schematic view of an additional embodiment of a hematocrit measurement device.
Figure 10B:
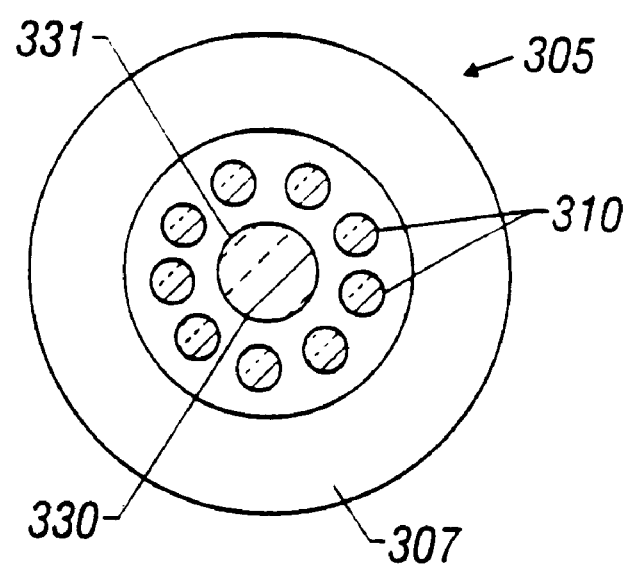
FIG. 10B is a top view of the illumination module of the device of FIG. 10A.

Referring to FIGS. 10A and 10B, another embodiment of a hematocrit measuring device 300 for measuring a reflection spectrum from a sample 500 includes a circular array of light-emitting diode (LED) radiation sources 310 for providing optical radiation, as described above.

LEDs 310 are mounted inside a cover housing 303. Cover housing 303 is preferably composed of an optically transparent material, such as glass or plastic. A cover 307 is attached to cover housing 303 and is preferably made from aluminum. Cover 307 includes a series of portholes 304 positioned above each LED so that radiation 311 can pass through cover 307 and onto sample 500.

The device 300 includes interior detector 350 and exterior detector 330 for detecting radiation. Exterior detector 330 is attached to cover 307 within a central bore 331 of cover 307.

Interior detector 350 is attached to bottom surface 306 of container 303. As the sample is irradiated, a portion 390 of the radiation emitted by the LED propagates to a back surface 308 of top cover 307 and is reflected towards the interior detector 350. In this way, the interior detector 350 monitors the optical output emitted from the LEDs. Radiation detected by the interior detector is used to determine a reference spectrum which allows intensity variations from the various LEDs to be accounted for.

Electrical power supplied to each LED can be modulated by the modulation system 410 to cause each LED to emit radiation for a specific time period during which the LED is modulated by a square, sine or pulse function synchronized with control clock 420. Radiation reflected from either sample 500 or back surface 308 has the same modulation frequency as the LED's modulation frequency. Radiation detected by exterior detector 330 is sent to phase-sensitive detection electronics, such as a lock-in amplifier 401. Radiation detected by interior detector 350 is sent to phase-sensitive detection electronics, such as lock-in amplifier 402. The modulation signal of control clock 420 is used by lock-in amplifiers 401, 402 to detect the reflected modulated radiation. The analog signals from lock-in amplifiers 401, 402 are sent to a ratiometer 403 to determine the analog reflectance signal 407 (ratio of the exterior detected radiation to the interior detected radiation). In some cases, ratiometer 403 can be incorporated into lock-in amplifier 401. Analog reflectance signal 407 is sent to an acquisition card 405 which converts analog reflectance signal 407 to a digital reflectance signal 408. Digital reflectance signal 408 is sent to a computer 430 to determine, as described above, the hematocrit of sample 500. Lock-in amplifier 401 and 402 include digital signal processing functions and may output digital signals.

LEDs 310 are commercially available and uniformly span the 500–1100 nm range with emission band widths of about 30–100 nm for each LED. The LED probe of FIGS. 10A and 10B could be held directly against a patients wrist or other sampling area to measure blood hematocrit.

Figure 11A:
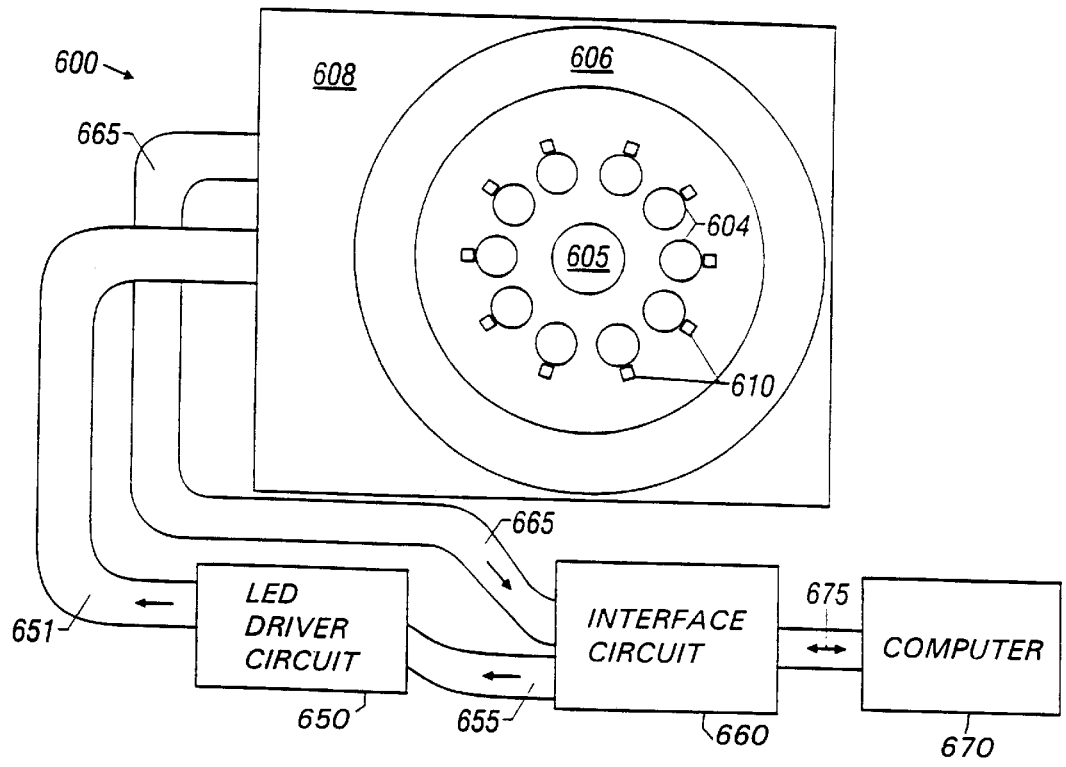
FIG. 11A is a top view of an additional embodiment of an integrated hematocrit measuring device.
Figure 11B:
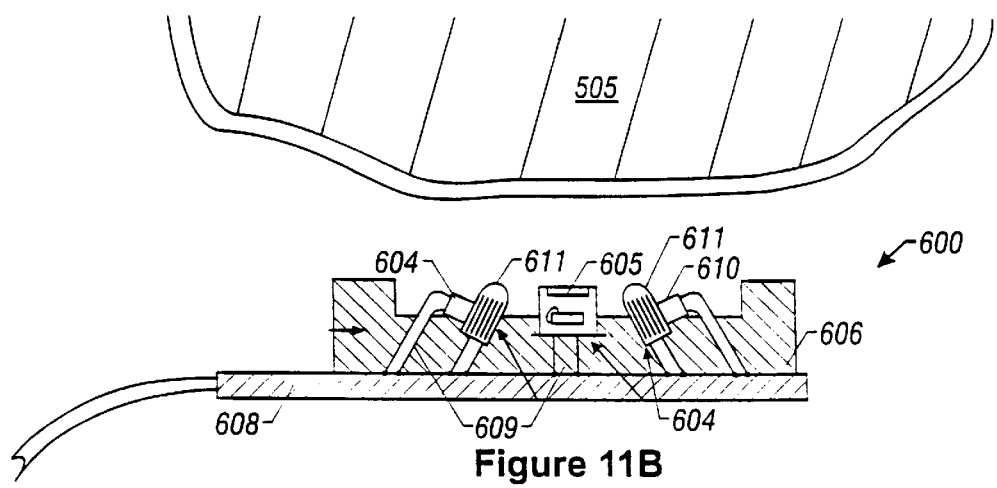
FIG. 11B is a side view of the integrated hematocrit measuring device of FIG. 11A.

FIGS. 11A and 11B show an integrated, self-contained hematocrit measuring device 600 for measuring a reflection spectrum from a sample 505. The hematocrit measuring device 600 features a circular array, e.g., typically at least seven, of light-emitting diode (LED) radiation sources 604, for providing optical radiation, as described above.

Figure 11C:
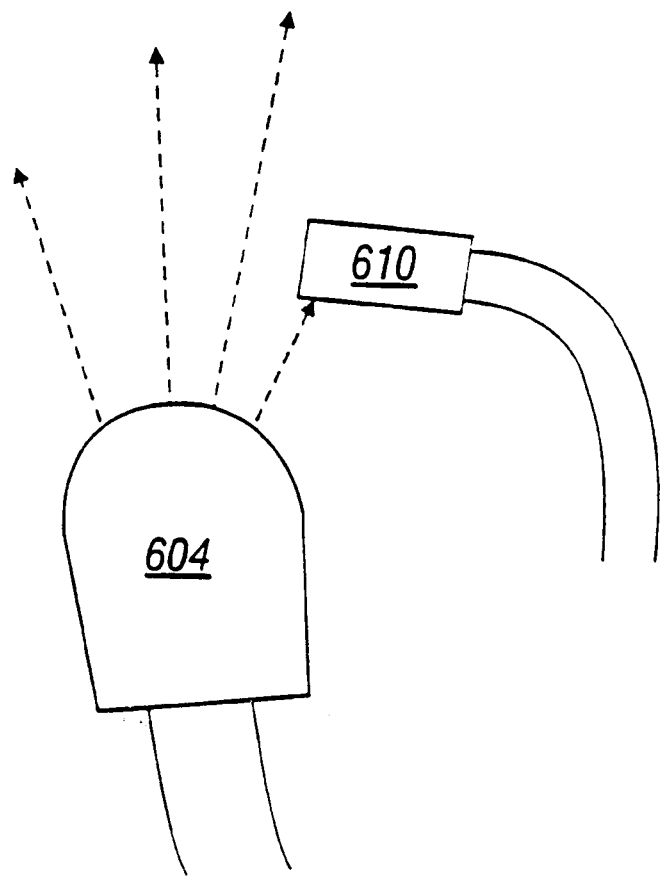
FIG. 11C is view of a LED and reference detector of the measuring device of FIG. 11A.

Device 600 includes a reflectance detector 605 and a series of reference detectors 610. LEDS 604 and detectors 605, 610 are mounted by connections 609 onto a printed circuit board 608. Reference detectors 610 are mounted on the side of each LED to measure and correct for variations in the LED intensity due to temperature, aging, or electrical power source drifts. FIG. 11C shows an alternate mounting position for reference detectors 610 which allows more light to reach reference detectors 610.

LEDs 604 and detectors 605, 610 are partially encapsulated or mounted in a polymer support 606, at an angle with respect to printed circuit board 608 of about 20 degrees. Reflectance detector 605 is preferably centrally located, e.g., center at about 4 mm from the optical axis of each LED 604, on circuit board 608. The LEDs are preferably in polymer packages with molded-on lenses 611 for collimating the output light. Polymer support 606 defines an outer lip 615 to fix the distance between sample 505 and hematocrit measuring device 600.

The associated electronic circuits of the self-contained hematocrit measuring device 600 include a LED driver circuit 650, an interface-circuit 660 and a computer 670. LED driver circuit 650 provides modulated current, e.g., square wave or sine wave or pulse modulation, e.g., at 1 kHz, through a drive cable 651 to drive LEDs 604. Interface circuit 660 performs analog/digital conversion of incoming detector signals traveling through a detector cable 665. Interface circuit 660 receives experimental parameter signals, e.g., modulation frequency, data acquisition initiation, and data acquisition termination, from computer 670 through a processor cable 675, and transmits digital signals to LED driver circuit 650 through a control cable 655.

Signal processing, including lock-in detection or gated integration, can be performed in computer 670 coupled to the interface circuit 660 or in analog circuits in interface circuit 660. The detector signal can also go through a preamplifier (not shown) located either on each detector 605, 610 or on interface circuit board 606. Alternatively, the associated electronic circuits including LED driver 650, interface circuit 660, and computer 670 are mounted external to hematocrit device 600 and coupled with a multi-element electrical cable (not shown).

Figure 12A:
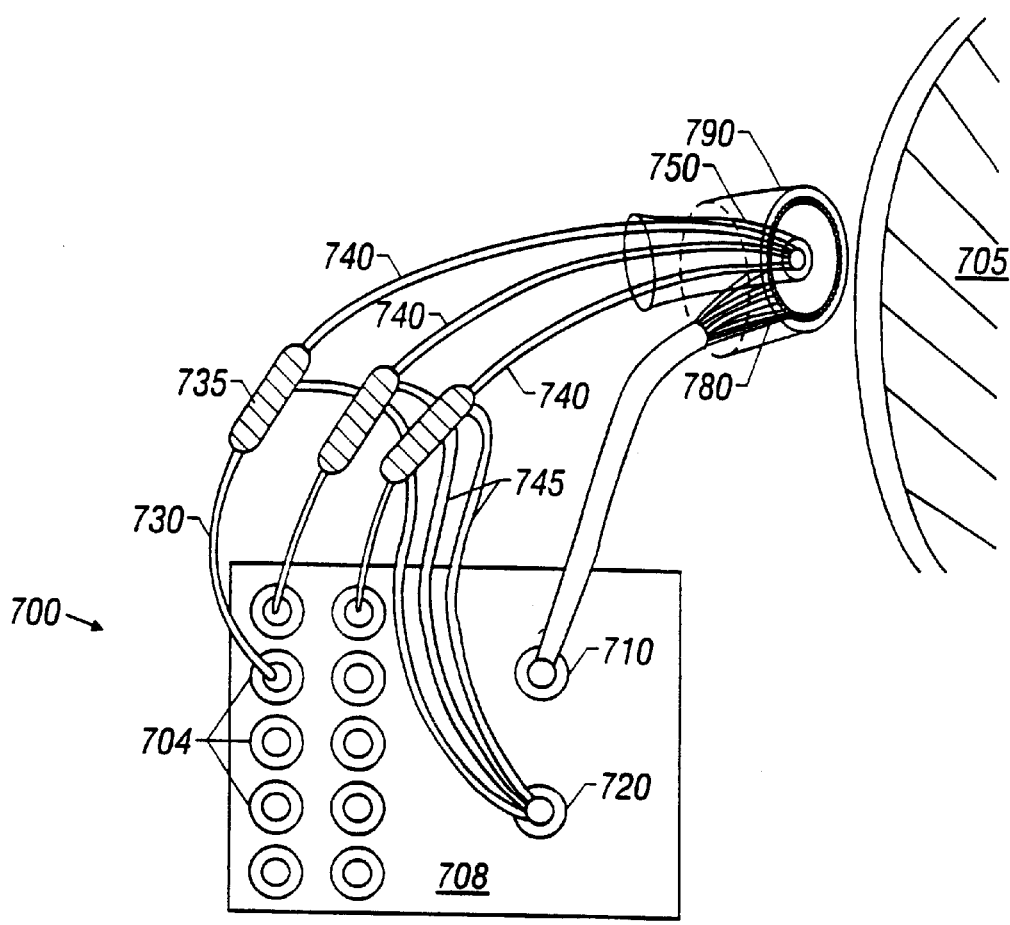
FIG. 12A is a top view of an additional embodiment of a new integrated hematocrit measuring device.
Figure 12B:
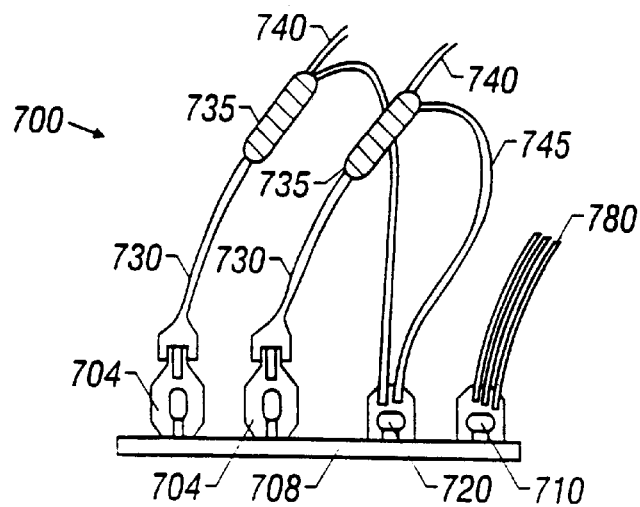
FIG. 12B is a side view of the integrated hematocrit measuring device of FIG. 12A.

FIGS. 12A and 12B show a hematocrit measuring device 700 for measuring a reflection spectrum from a sample 705. The hematocrit measuring device 700 features an array of, e.g., at least seven, light-emitting diode (LED) radiation sources 604, for providing optical radiation, as described above.

Device 700 includes a reflectance detector 710 and a reference detector 720. LEDs 704 and detectors 710, 720 are integrated onto a printed circuit board 708.

Each LED 704 is coupled to one of a series of single optical fiber elements 730 and then to a fiber splitter 735 which sends an amount, e.g., 60%, of the fiber coupled LED light through a probe fiber 740 to a probe tip 790 and the remaining, e.g., 40%, of the light through reference fibers 745 to reference detector 720. Reference detector 720 is coupled to one optical fiber from each LED. The fiber-optic coupling is shown for only three of the ten LEDS to simplify the diagram. All of LEDs 704 have similar fiber coupling.

Probe fibers 740 from fiber splitter 735 are combined into a single fiber bundle 750 terminating at a probe tip 790. Light from fiber bundle 750 illuminates sample 705. The return reflected light is received by an array of, e.g., twenty-five, single fibers 780 configured in a ring 781 concentric about fiber bundle 750. For simplicity, only three of the twenty-five fibers connected to the circular reflectance array are shown in FIG. 12b. The spacing between the center illuminating fiber bundle 750 and the outer fiber ring 781 is preferably 2–4 mm when the probe tip 790 has a diameter of 5 mm.

Figure 12C:
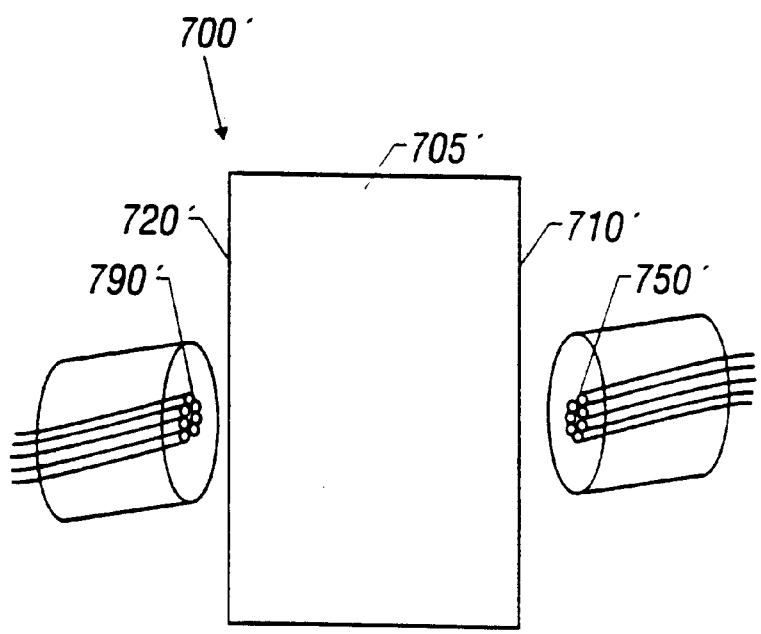
FIG. 12C is a side view of a variation of the integrated hematocrit measuring device of FIG. 12A, used to record a transmission spectrum.

Hematocrit measuring device 700 can be modified, as shown in FIG. 12C, to measure the transmission through a sample 705', e.g., an ear lobe or the webbing between the thumb and the first finger. The transmission device 700' includes a fiber bundle 750' (10 element bundle as describe above) and a receiving fiber bundle 790' ( 25 element bundle, as described above). Fiber bundle 750' illuminates one side 710' of sample 705' and receiving fiber bundle 790', positioned parallel with respect to fiber bundle 750' and on the opposite side 711' of sample 705', receives transmitted LED light. The receiving bundle 790', for example, has a larger diameter than the bundle 750' used for illumination.

Figure 13A:
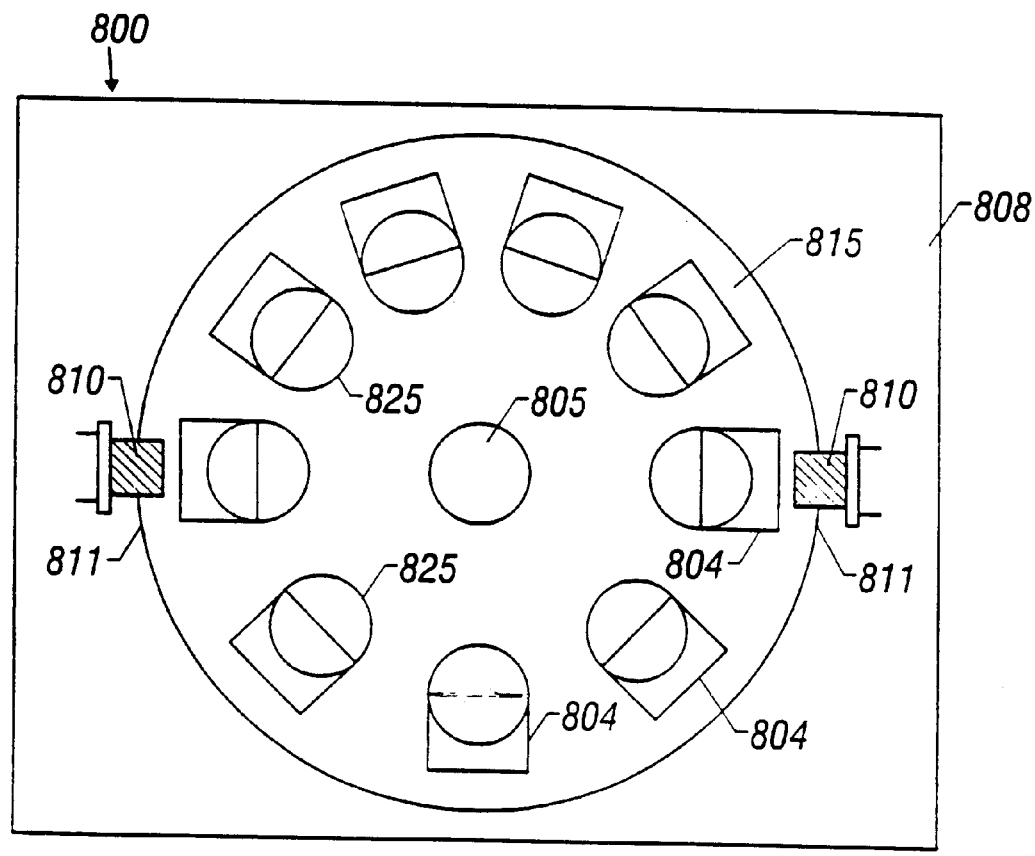
FIG. 13A is a top view of an additional embodiment of a new integrated hematocrit measuring device.
Figure 13B:
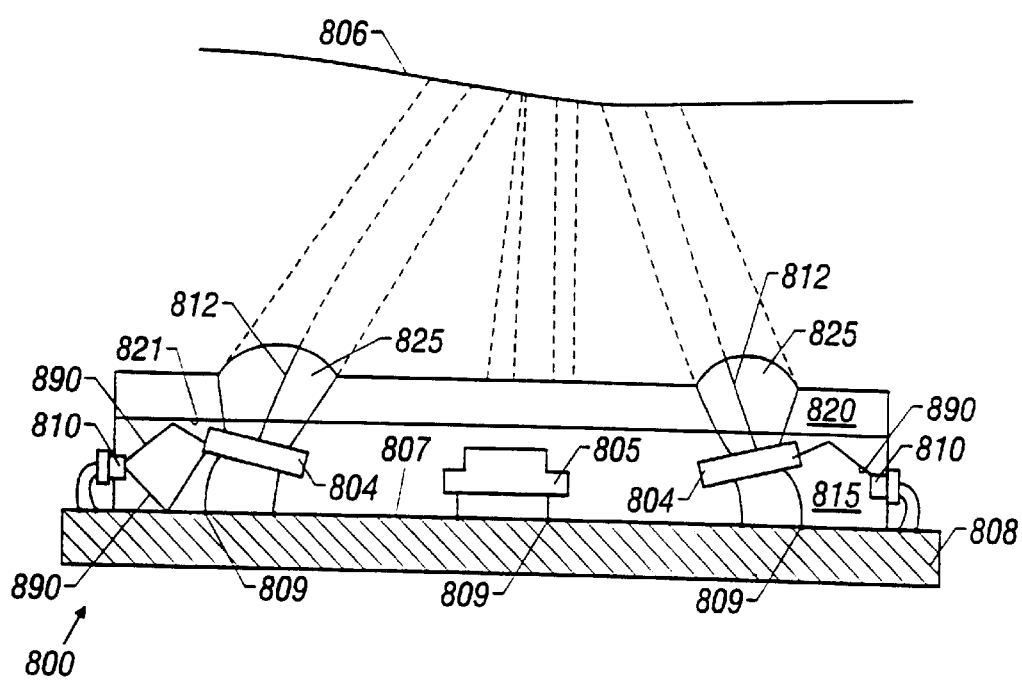
FIG. 13B is a side view of the integrated hematocrit measuring device of FIG. 13A.

FIGS. 13A and 13B show another embodiment of an integrated, self-contained hematocrit measuring device 800 for measuring a reflection spectrum from a sample 806. The hematocrit measuring device 800 features a circular array of, e.g., at least seven, light-emitting diode (LED) radiation sources 804, for providing optical radiation, as described above.

Device 800 includes a reflectance detector 805 and two reference detectors 810. LEDs 804 and detectors 805, 810 are integrated onto a printed circuit board 808. LEDs 804, reflectance detector 805, and reference detectors 810 are encapsulated by a support layer 815, preferably made of a clear polymer material. Reference detectors 810 are mounted along the perimeter 811 of support layer 815 to measure and correct for variations in the LED intensity due to temperature, aging or electrical power source drifts.

LEDs 804 are mounted at an angle with respect to printed circuit board 808, e.g., 20–40 degrees. The reflectance detector 805 is centrally located with respect to the LEDs at a distance, e.g., 2–4 mm, from the center of the optical axis of each LED 804. Support layer 815 is covered by a lens array 820 preferably made from a polymer material with an anti-reflection coating. Lens array 820 contains a series of molded lenses 825 used to collimate output light from LEDs 804.

During operation, optical radiation 812 from each LED is emitted in all directions. A majority of the radiation 812 passes through the molded lenses 825, is collimated and irradiates sample 500. This radiation is partially reflected by the sample towards reflectance detector 805.

As sample 806 is irradiated, a portion 890 of the radiation emitted by each LED is reflected towards reference detectors 810 by a top surface 807 of printed circuit board 808 and by top and bottom surfaces of lens array 820. In this way, reference detector 810 monitors the optical output emitted from LEDs 804.

In other embodiments, optical signals from arteries are isolated by synchronizing the optical signal acquisition with the pulsatile flow of arterial blood. In this arrangement, a second optical sensing probe consisting of a single LED and detector pair would sense the arterial pulse and would be used to gate the near-infrared spectrometer data collection to the peak of the pulse. The output signal from the optical detector is translated into absorbance by a computer attached to the sensor.

The invention will be further described in the following examples, which do not limit the scope of the invention described in the claims.

EXAMPLES
Optical Measurements Determining Hematocrit

The feasibility of non-invasively measuring hematocrit has been demonstrated. Referring to FIG. 14, the near-infrared reflectance spectra of pig blood 1010 were measured with a bifurcated collinear optic fiber bundle 1000 over the 575–1100 nm spectral range. The fiber bundle probe employed for reflectance measurement consisted of six 200 $\mu$m illuminating fibers 1020 disposed radially about one 100 $\mu$m centrally located receiving fiber 1030. A 5 W miniature tungsten halogen lamp 1025 was used as the illumination source. The spectra were measured with a miniature computer card spectrometer 1050 with a diode array detector, not shown.

About 500 ml of whole blood was obtained from a pig. The blood sample was centrifuged at 3000 rpm for 15 min and 200 ml of the top layer plasma was removed. The centrifuged blood was then re-suspended to make a 300 ml pre-concentrated blood sample. The pre-concentrated blood sample was diluted by varying amounts with a saline/heparin solution to prepare a set of 20 blood samples with varying hematocrit. The reference measurement of hematocrit used to create the model for hematocrit was performed both by a conventional capillary method, and by electrical conductivity using a commercial blood gas machine for each of these samples.

A set of 10 hematocrit measurements were taken and averaged for each sample using capillary tubes. The measured hematocrit ranged from 1.7% to 26.9% for the 20 samples. The overall standard deviation for all the capillary hematocrit measurements was 0.4%, while the standard deviations for the 10 repeat capillary hematocrit measurements for the individual samples ranged from 0.1% to 0.9%. One blood gas machine measurement was taken for each sample and hematocrit (conductivity) was obtained. Table I lists the ranges for hematocrit. The hematocrit measured by conductivity are lower than the capillary tube measurements by an average of 4.4% (hematocrit units). Therefore, the capillary tube measurements are used as reference values to derive a multivariate calibration model for non-invasivee determination of hematocrit.

A cuvette holder 1060 and a quartz cuvette 1061 was used through the entire experiment. Bifurcated collinear fiber optic bundle 1000 used as a reflectance probe was mounted against a wall 1062 of quartz cuvette 1061, which was used to hold the blood sample. Samples were measured in a randomized order to eliminate any possible correlation between the spectrometer drift and the component concentration. All spectra were collected in single-beam format and were converted to absorbance units (i.e., log(1/R)) using the blank cuvette as the reference. The acquisition time for the spectra-was 36 seconds.

TABLE I

Ranges of Hematocrit for the 20 blood samples.

|  | Hct (%) |
|---|---|
| Min. | 0 |
| Max. | 24 |
| Change | 24 |

Figure 15:
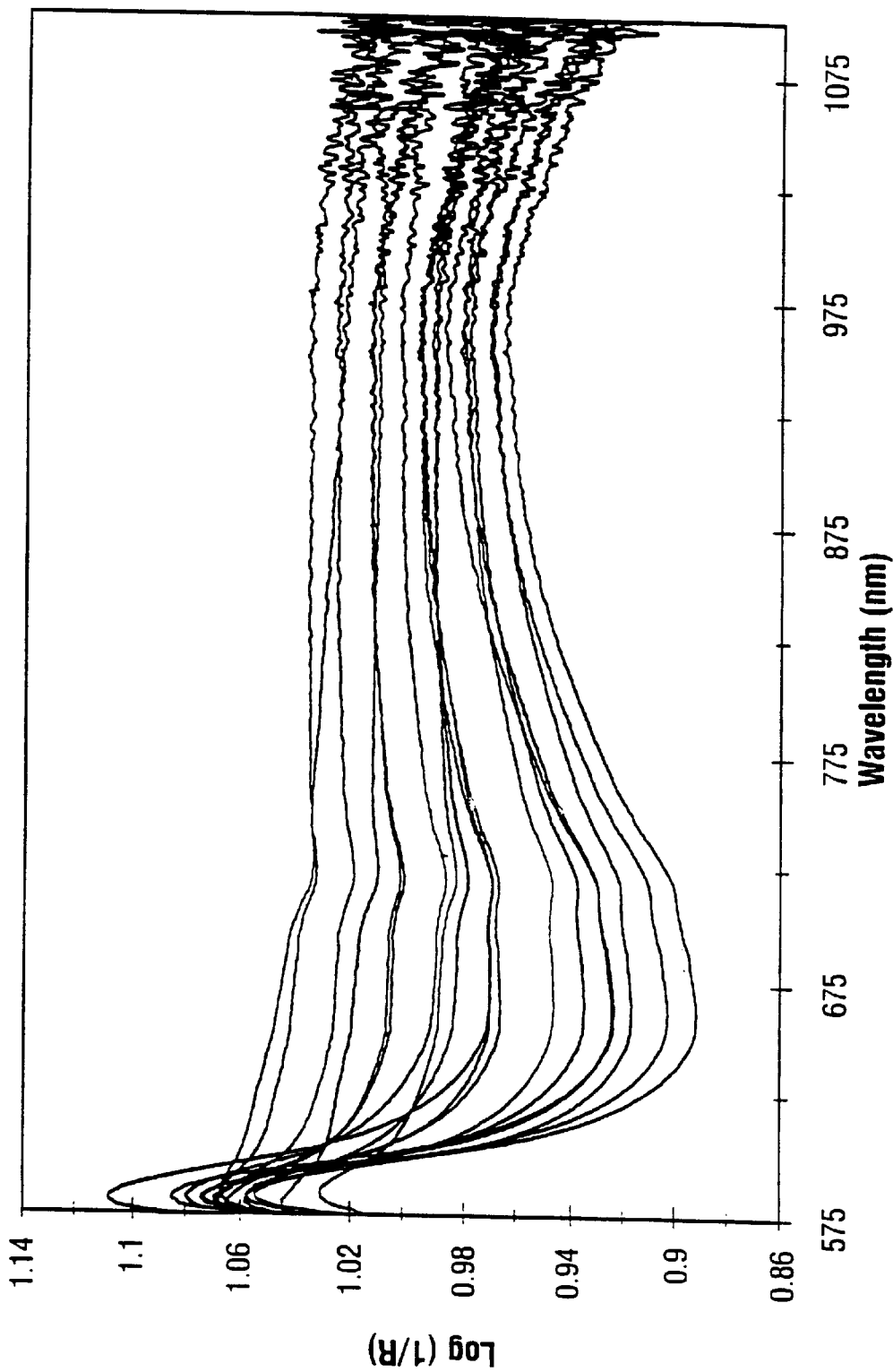
FIG. 15 is a series of reflection spectra collected with the hematocrit measuring device of FIG. 14 from extracted porcine blood having varying hematocrit.

FIG. 15 shows reflectance spectra in absorbance units for the 20 samples as the hematocrit varies from 1.7% to 26.9%. The prominent spectral features are attributed to the absorption due to hemoglobin and water presented in the sample. The sharp peak near 576 nm and the wide band over the region of 750–1100 nm is the signature of hemoglobin. Since only the near-infrared radiation (700–1100 nm) easily penetrates bone and tissue and the spectral noise becomes significant above 1000 nm, only the spectral region of 700–1000 nm was used to derive the calibration models for the non-invasivee spectral determination of hematocrit and the other blood components.

Partial least-squares with cross-validation techniques were used to establish the calibration relationship between the capillary tube/blood gas machine reference measurements and the near-infrared spectral data. The calibration models were evaluated by the linear correlation coefficient ($R^2$) and the standard error of prediction (SEP). For a perfect calibration model, the $R^2$ would equal 1 and the SEP would be 0. The SEP is limited by the spectral noise and the standard error of the reference measurements, i.e., the standard error of the capillary tube measurements for hematocrit.

Table II lists the PLS cross-validated calibration results. The reference hematocrit values were obtained from capillary tube readings. The PLS calibration was performed on the whole spectral region of 700–1000 nm containing 601 wavelengths (equally spaced between 700–1000 nm) and on a set of eight selected wavelengths (700, 735, 760, 815, 880, 900, 940, and 1000 nm). The results shown in table II indicate that the eight wavelengths would yield an accuracy equivalent to that of the whole spectral region of 601 wavelengths. The accuracy of the near-infrared hematocrit measurements is comparable to that of the capillary tube measurements, with an SEP of 1.2% and an $R^2$ of 0.98.

TABLE II

PLS calibration results for Hematocrit using 601 and 8 wavelength intervals.

|  | 601 Wavelengths | | 8 Wavelengths | |
|---|---|---|---|---|
|  | SEP | $R^2$ | SEP | $R^2$ |
| Hct (%) | 1.20 | 0.98 | 1.16 | 0.98 |

Figure 14A:
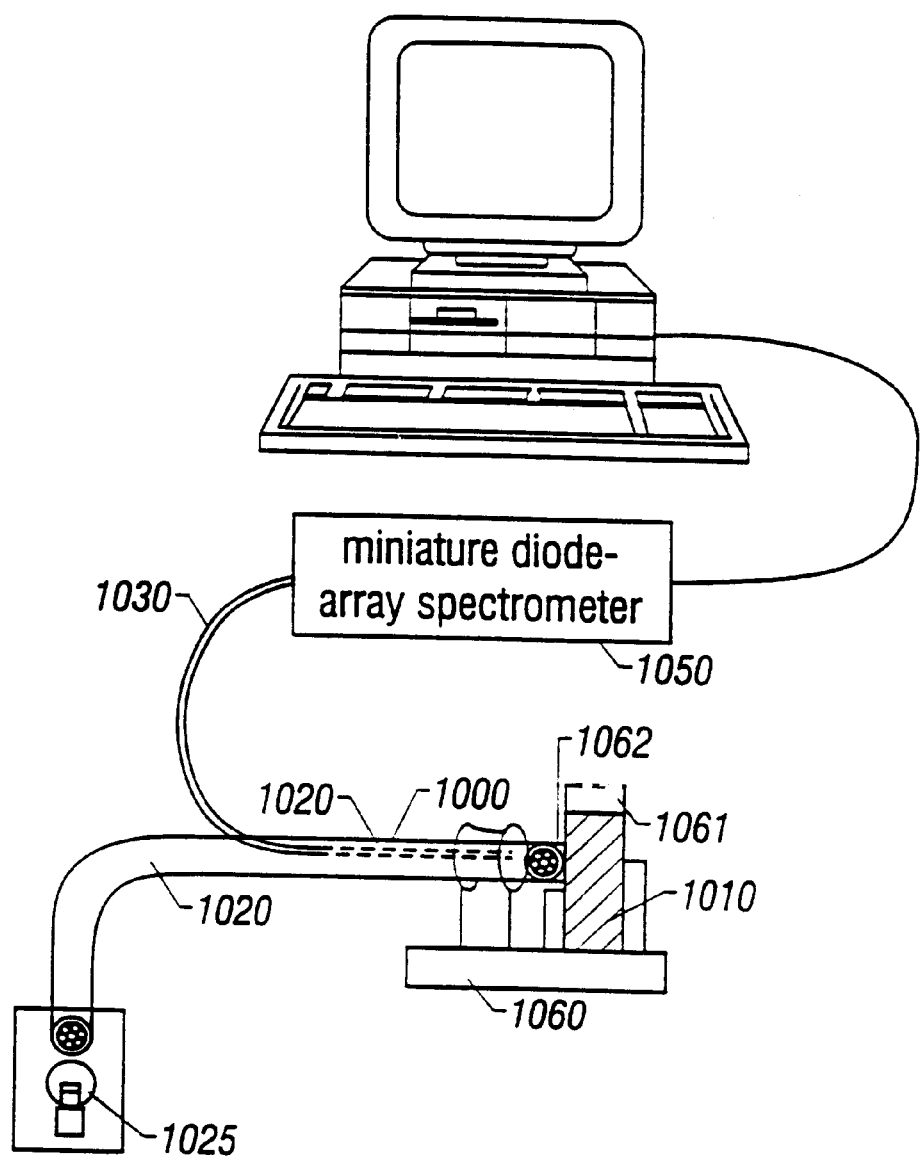
FIG. 14A is a hematocrit measuring device used to determine hematocrit from porcine blood.
Figure 14B:
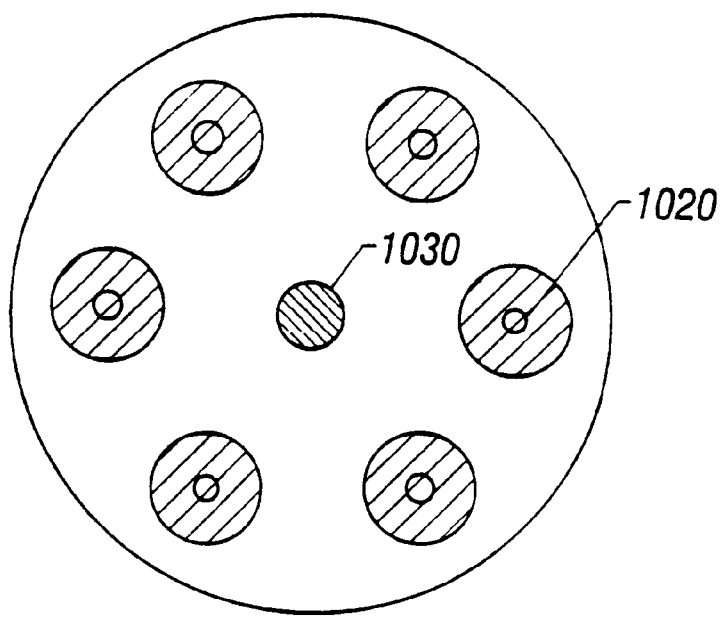
FIG. 14B is a cross-sectional view of the delivery and signal cables used in the hematocrit measuring device of FIG. 14A.
Figure 16:
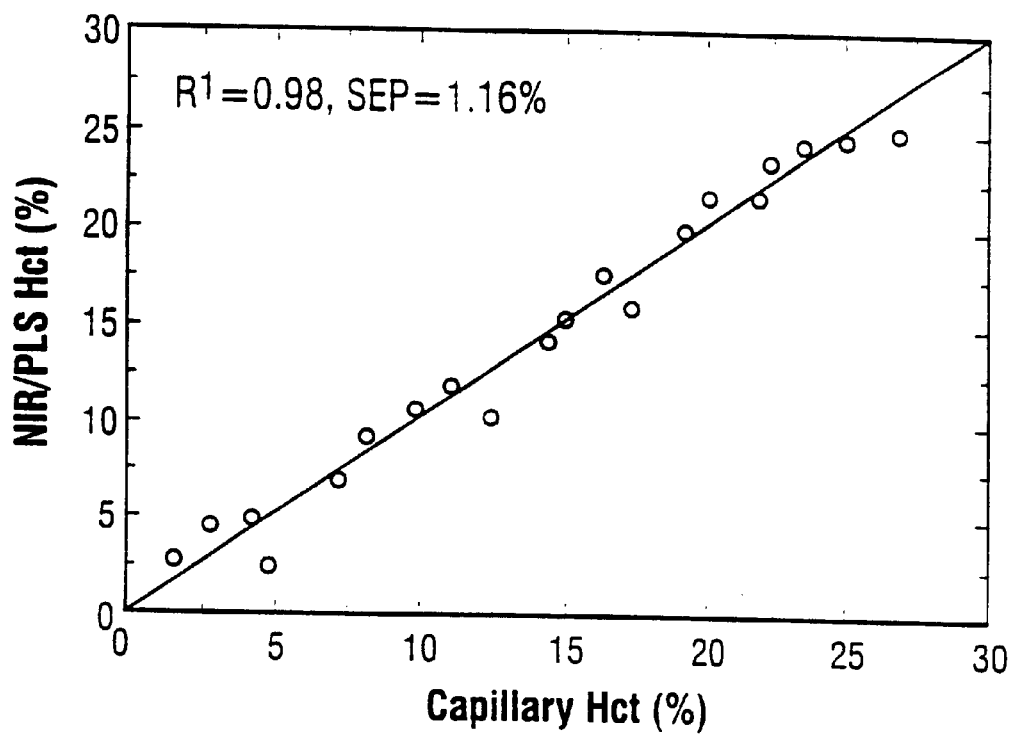
FIG. 16 is a plot of predicted hematocrit as a function of actual hematocrit determined by the hematocrit measuring device of FIG. 14.

FIG. 16 shows a plot of PLS predicted versus capillary tube measured hemtocrit. The capillary tube measurements have an 0.4% overall standard deviation in the 10 repeat measurements for each sample which is a major factor contributing to in the 1.2% SEP value for the near-infrared determined hematocrit. In addition, the fiber optic probe 1000 was not optimally designed for this experiment. The spacing of the individual fibers used to conduct these measurements was approximately 40 microns. Referring to FIG. 14B, a separation of 1–5 mm, of the receiving fiber 1030 from the illuminating fibers 1020, arranged in a radially symmetric array about receiving fiber 1030, facilitates obtaining adequate depth penetration into the tissue being sampled by the light received by the receiving fiber 1030. If the spacing of the illumination fibers 1020 from the receiving fiber 1030 is too small then the majority of the reflected light signal received by receiving fiber 1030 will originate at the air/tissue interface which does not contain a significant amount of blood. Also, the geometry of the fiber optic probe is likely to be a limiting factor in the noise level in the spectral data obtained.

The performance of integrated, hematocrit measuring device 300, with LED sources, as shown in FIG. 10A and FIG. 10B, has been evaluated on a pig experiencing hemorrhagic shock. Hematocrit measuring device 300 including nine LED's was used to collect optical spectra of porcine blood in the abdominal wall muscle. Each LED of device 300 has a different central wavelength located within the 700–1100 nm wavelength range. A bifurcated collinear optic fiber bundle 1000 without the cuvette holder 1060 and cuvette 1061, as shown in FIG. 14A, was also placed on the abdominal wall of the pig to collect optical spectra of porcine blood. Optical spectra were recorded using device 1000 at 700 distinct wavelengths between 575 and 1050 nm to investigate the importance of wavelengths shorter than 700 nm on hematocrit measurements. Several blood samples were extracted from the pig during hemorrhagic shock and hematocrit was measured by a standard method, e.g., capillary tube.

Figure 17:
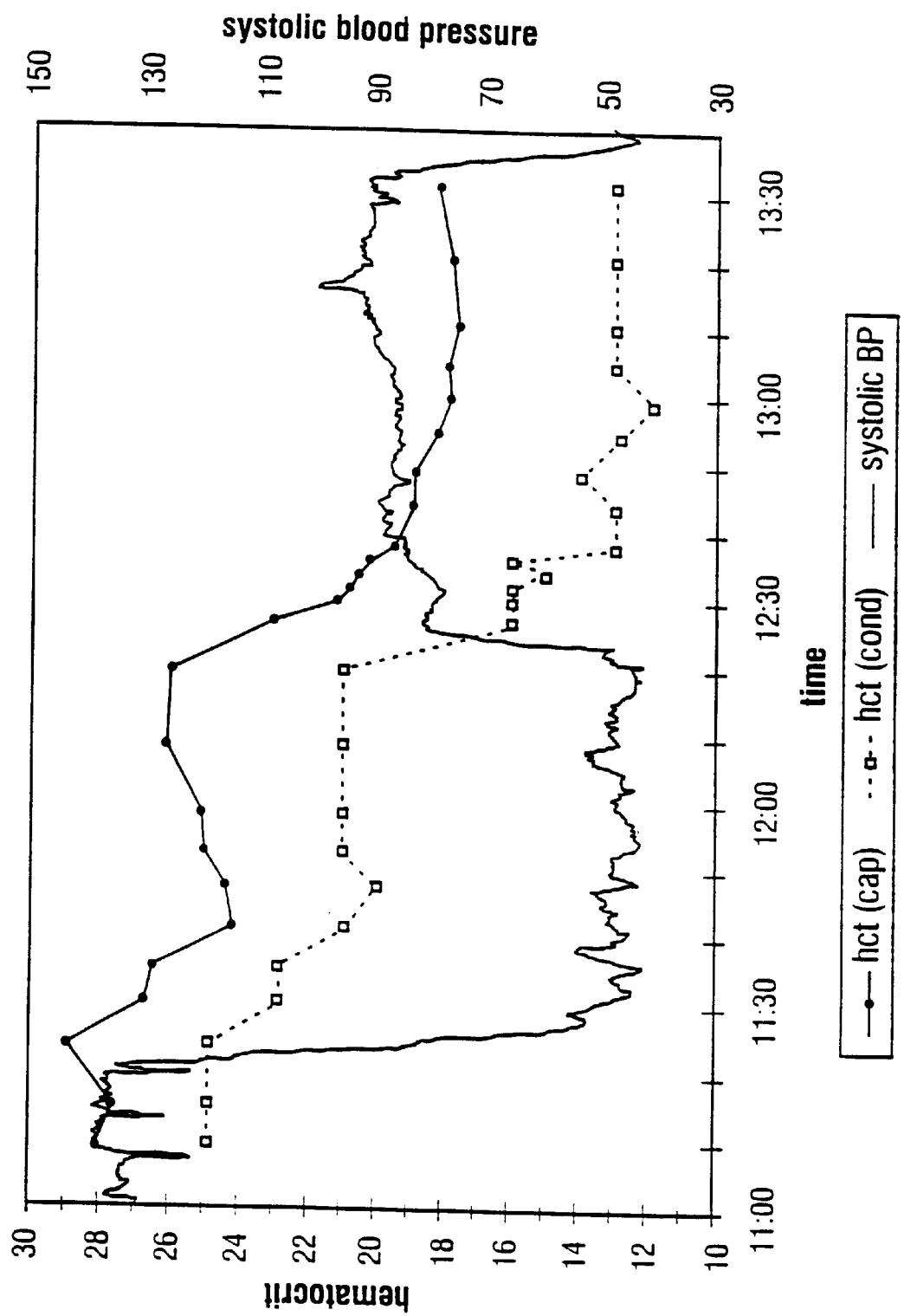
FIG. 17 is a plot of capillary hematocrit measurements, conductivity hematocrit measurements, and systolic blood pressure as a function of time.

Hemorrhagic shock was initiated by withdrawing enough blood to lower the pig's systolic blood pressure to approximately 40 mm Hg. The blood pressure was maintained near 40 mm Hg for 45 minutes, at which time the pig was resuscitated with a blood/lactated ringers mixture. The pig's recovery was monitored for 60 minutes, adding lactated ringers as needed. Two 1.0 ml samples of blood were withdrawn into heparin coated syringes from a catheter placed in the pig's left femoral artery. One of the samples was analyzed in an Instrumentation Labs blood gas analyzer where hematocrit was measured using the conductivity method. The other sample was divided into 10 heparin coated microcapillary tubes. The tubes were centrifuged for 5 minutes and analyzed for hematocrit using a microcapillary reader. Blood samples were drawn approximately every 5 minutes. However near the end of the shock period and the end of the recovery period, samples were taken every 10 minutes because hematocrit does not change during these periods. Alternatively, during the resuscitation period, blood samples were drawn every 2 minutes because hematocrit changes rapidly. A plot of hematocrit, determined by the capillary method and by the conductivity method, as a function of time is shown in FIG. 17, along with blood pressure values which indicate the state of shock and recovery.

Optical spectra were recorded continuously during the experiment with both devices 300, 1000. Optical spectra recorded at the time blood was drawn from the pig were matched with the hematocrit values of the drawn blood determined by the capillary method. The Partial Least Square (PLS) method, as described above, was then used to create the calibration model relating hematocrit to optical spectra. PLS models were first created using all spectra. If a spectrum was identified as an outlier, the spectrum was removed and a new model was created with the outliers eliminated. The analysis was done for device 300 using all 9 LED's or only 7 LED's with the shortest wavelength's. Four wavelength regions, both including and excluding the longer wavelengths, were analyzed with device 1000. The longer wavelengths contain information from the water bands. The shorter wavelengths include additional hemoglobin information. The results are included in Table III.

TABLE III

| Device | Range | No. of Samples | | SEP (% hct) | | $R^2$ | | Factors | |
|---|---|---|---|---|---|---|---|---|---|
|  |  | All | Outliers removed | All | Outliers removed | All | Outliers removed | All | Outliers removed |
| 300 | 1–7 | 25 | 22 | 1.45 | 0.86 | 0.866 | 0.938 | 1 | 1 |
|  | 1–9 | 25 | 22 | 1.50 | 0.89 | 0.856 | 0.933 | 1 | 1 |
| 1000 | 581–1094 nm | 25 | 22 | 1.47 | 0.82 | 0.862 | 0.944 | 4 | 4 |
|  | 700–1094 nm | 25 | 21 | 2.87 | 1.31 | 0.472 | 0.858 | 2 | 3 |
|  | 700–1000 nm | 25 | 23 | 1.86 | 1.74 | 0.777 | 0.793 | 7 | 9 |
|  | 581–1000 nm | 25 |  | 0.97 |  | 0.940 |  | 8 |  |

Figure 18:
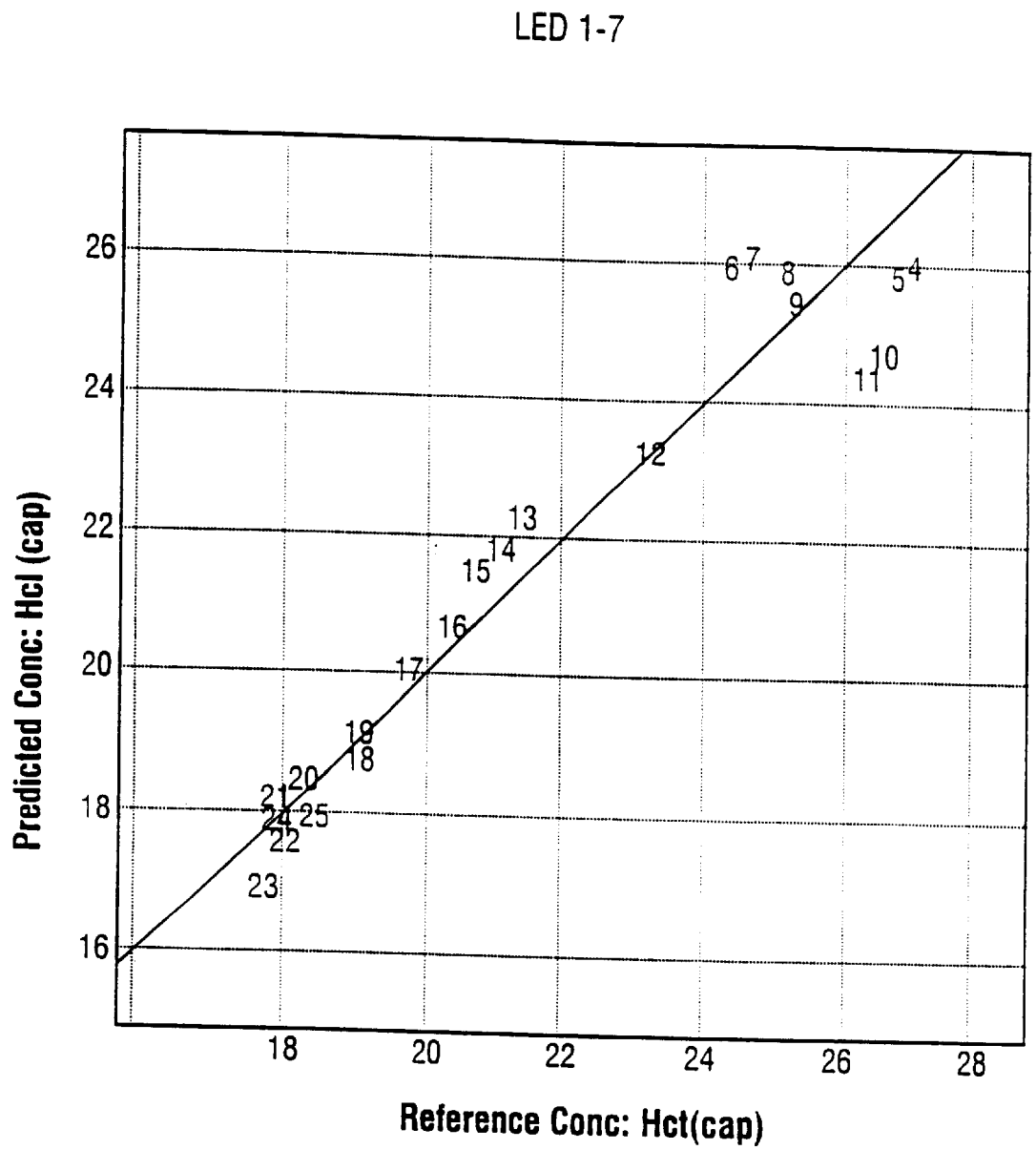
FIG. 18 is a plot of predicted hematocrit non-invasively measured on a pig, with outliers removed, as a function of actual hematocrit, determined by the hematocrit measuring device of FIG. 5.
Figure 19:
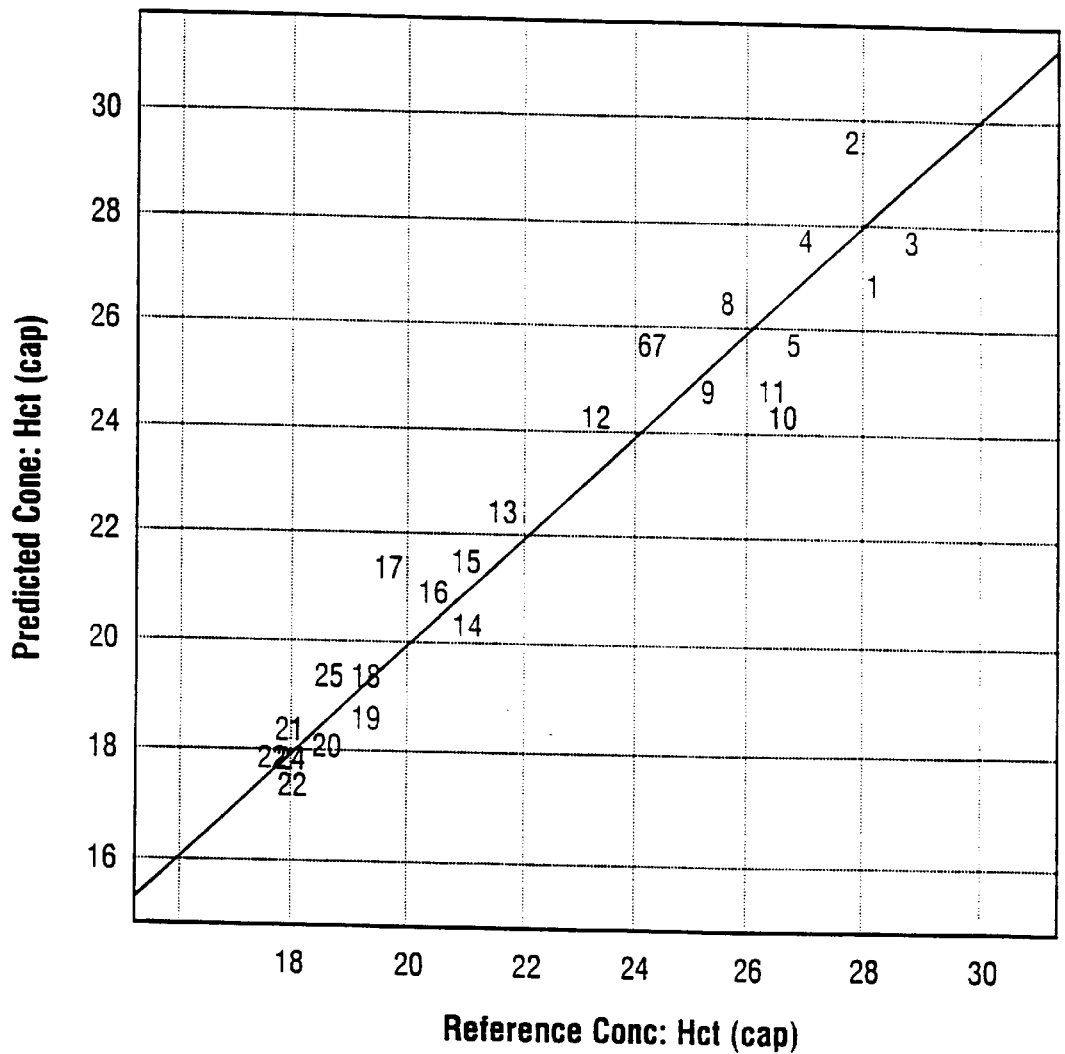
FIG. 19 is a plot of predicted hematocrit non-invasively measured on a pig as a function of actual hematocrit.

The best results were obtained by excluding wavelengths above 1000 nm and by including wavelengths below 700 nm. FIG. 18 and FIG. 19 show the predicted versus reference hematocrit values obtained for device 300 using 7 LED's (1–7 model) with outliers removed, and for device 1000 using wavelengths between 581–1000 nm (581–1000 nm model), where there were no outliers identified. The Standard Error of Prediction (SEP) for both of these models is under 1%. These results, however, are limited by the reference hematocrit measurement which showed an average standard deviation of 0.51% for each replicate set of 10 readings.

Other Embodiments

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for determining blood hematocrit, the device comprising:

an array of light sources for delivering radiation to a sample;

a power supply;

a modulation system in electrical contact with each of the light sources and the power supply, the modulation system configured to modulate electrical power delivered from the power supply to each of the light sources at a unique modulation frequency;

a detection system comprising a first optical detector and a plurality of second optical detectors, the first optical detector being configured to receive radiation from the sample, and, in response generating a first set of radiation-induced electrical signals, each corresponding to radiation delivered from a separate light source to the sample, and the plurality of second optical detectors each being configured to detect radiation directly from one of the light sources, and, in response generating a second set of radiation-induced electrical signals, each corresponding to radiation delivered from a separate light source, a signal processor for receiving the first set of electrical signals and, in response, generating a first set of digital electrical signals;

a microprocessor configured to receive the first set of digital electrical signals to calculate blood hematocrit, the microprocessor being programmed to first process the first set of digital electrical signals to determine a first spectrum and then processing the first spectrum or a spectrum determined from the first spectrum with a mathematical model to determine blood hematocrit.

2. A device of claim 1, wherein the detection system further includes phase-sensitive detection electronics in electrical contact with the first optical detector and the plurality of second optical detectors to detect radiation generated at the unique modulation frequency, the phase-sensitive detection electronics being incorporated in an amplifier.

3. A device of claim 1, wherein the signal processor is configured to perform signal averaging of the electrical signals.

4. A device of claim 1, wherein the microprocessor is programmed to perform signal averaging of the electrical signals.

5. A device of claim 1, wherein the plurality of second optical detectors comprises two optical detectors.

6. A device of claim 1, wherein there is an equal number of second optical detectors and light sources.

7. A device of claim 1, wherein the signal processor is additionally configured for receiving the second set of electrical signals and, in response, generating a second set of digital electrical signals.

8. A device of claim 7, wherein the microprocessor is further programmed to process the second set of digital electrical signals to determine a reference spectrum and then calculate a ratio between the reference spectrum and the first spectrum.

9. A device of claim 1, wherein the microprocessor is further programmed to calculate the mathematical model prior to processing the first set of digital electrical signals.

10. A device of claim 1, further comprising a molded lens array to collimate output light from the array of light sources.

11. A device of claim 1, wherein the light sources deliver visible and near-infrared light.

12. A device of claim 11, wherein the visible and near-infrared light comprises radiation between 500 nm and 1100 nm.

13. A device of claim 11, wherein each light source delivers radiation having a bandwidth of between about 0.1 and 100 nm.

14. A device of claim 1, wherein each light source comprises a light-emitting diode.

15. A device of claim 1, wherein each light source comprises a diode laser.

16. A device of claim 1, wherein the array of light sources comprises seven light sources.

17. A device of claim 1, wherein the light sources are adapted to deliver optical wavelengths selected to be affected by a plurality of red blood cell constituents.

18. A device of claim 17, wherein the optical wavelengths are affected by absorption and scattering from the plurality of red blood cell constituents.

19. A device for determining blood hematocrit, the device comprising:

a mount;

an array of light sources attached to the mount;

a fiber optic cable attached to each light source, the fiber optic cable including a delivery fiber for delivering radiation to the sample, a reference fiber for delivering radiation to a detection system, a beam splitter for splitting light into the delivery fiber and the reference fiber, and a signal fiber for delivering radiation reflected by the sample to a detection system;

a power supply electrically coupled to the mount;

a modulation system electrically coupled to the mount and arranged to modulate electrical power delivered from the power supply to each of the light sources;

a detection system comprising a first optical detector attached to the mount and coupled to the signal fiber for receiving radiation delivered from the sample, and, in response generating a first set of electrical signals, each corresponding to sample radiation delivered from a separate light source to the sample, and a second optical detector attached to the mount and coupled to each reference fiber for receiving radiation from each of the light sources, and, in response generating a second set of radiation-induced electrical signals, each corresponding to radiation delivered from a separate light source;

a signal processor electrically coupled to the mount for receiving the first set of electrical signals, and, in response to the radiation, generating a first set of digital signals, and for receiving the second set of electrical signals, and, in response to the radiation, generating a second set of digital electrical signals; and a microprocessor configured to receive the first set and the second set of digital signals and to calculate blood hematocrit, said microprocessor being programmed to process the first set of digital signals to determine a first spectrum and then processing the first spectrum or a spectrum determined from the first spectrum with a mathematical model to determine blood hematocrit of the sample.

20. A device of claim 19, wherein the microprocessor is further programmed to process the second set of digital electrical signals to determine a reference spectrum and then calculate a ratio between the reference spectrum and the first spectrum.

21. A device of claim 19, wherein a portion of the fiber optic cable comprises a delivery fiber bundle surrounded by radially disposed signal fibers in a region where the fiber optic cable delivers radiation to the sample.

* * * * *